US009492262B2

(12) United States Patent
Inoue

(10) Patent No.: US 9,492,262 B2
(45) Date of Patent: Nov. 15, 2016

(54) DEVICE FOR CAPTURING DEBRIS IN BLOOD VESSELS

(71) Applicant: Kanji Inoue, Kyoto (JP)

(72) Inventor: Kanji Inoue, Kyoto (JP)

(*) Notice: Subject to any disclaimer, the term of this patent is extended or adjusted under 35 U.S.C. 154(b) by 309 days.

(21) Appl. No.: 14/347,502

(22) PCT Filed: Sep. 26, 2012

(86) PCT No.: PCT/JP2012/074796
§ 371 (c)(1),
(2) Date: Mar. 26, 2014

(87) PCT Pub. No.: WO2013/047623
PCT Pub. Date: Apr. 4, 2013

(65) Prior Publication Data
US 2014/0236220 A1   Aug. 21, 2014

(30) Foreign Application Priority Data
Sep. 27, 2011   (JP) ................................. 2011-210244

(51) Int. Cl.
*A61F 2/01*   (2006.01)
*A61B 17/221*   (2006.01)

(52) U.S. Cl.
CPC .............. *A61F 2/01* (2013.01); *A61B 17/221* (2013.01); *A61F 2/013* (2013.01); *A61F 2002/016* (2013.01); *A61F 2230/001* (2013.01); *A61F 2230/0006* (2013.01); *A61F 2230/0067* (2013.01); *A61F 2230/0093* (2013.01)

(58) Field of Classification Search
CPC .................... A61B 17/221; A61B 2017/2212; A61F 2/01; A61F 2/013; A61F 2002/011; A61F 2002/016; A61F 2230/0067; A61F 2230/0093
See application file for complete search history.

(56) References Cited

U.S. PATENT DOCUMENTS

| 5,954,745 | A | | 9/1999 | Gertler et al. | |
|---|---|---|---|---|---|
| 6,142,987 | A | * | 11/2000 | Tsugita | A61F 2/01 604/500 |
| 6,277,138 | B1 | * | 8/2001 | Levinson | A61F 2/013 604/164.13 |
| 6,306,163 | B1 | * | 10/2001 | Fitz | A61B 17/22 606/198 |
| 6,355,051 | B1 | * | 3/2002 | Sisskind | A61F 2/013 606/200 |
| 6,361,545 | B1 | * | 3/2002 | Macoviak | A61B 17/12136 606/151 |
| 6,371,971 | B1 | * | 4/2002 | Tsugita | A61F 2/01 606/200 |

(Continued)

FOREIGN PATENT DOCUMENTS

| CN | 1331956 A | 1/2002 |
|---|---|---|
| JP | 2005506105 A | 3/2005 |

(Continued)

OTHER PUBLICATIONS

European Patent Office, Extended European Search Report Issued in Patent Application No. 12834893.5, May 4, 2015, Germany, 6 pages.

(Continued)

*Primary Examiner* — Ryan J Severson
(74) *Attorney, Agent, or Firm* — Alleman Hall McCoy Russell & Tuttle LLP

(57) ABSTRACT

Provided is a device for capturing debris in blood vessels, which enables a filter member to be smoothly recovered, and has a simple structure leading to an easy operation. For this purpose, provided is an elastic steel wire that, in a folded state, extends in a direction toward a base of a slide tube from a fore end part of a holding part in a ringlike elastic wire rod along an outer side of the slide tube.

13 Claims, 23 Drawing Sheets

(56) References Cited

U.S. PATENT DOCUMENTS

| | | | | |
|---|---|---|---|---|
| 6,425,909 B1* | 7/2002 | Dieck | A61F 2/013 | 606/200 |
| 6,558,406 B2* | 5/2003 | Okada | A61F 2/01 | 606/200 |
| 6,610,077 B1* | 8/2003 | Hancock | A61F 2/013 | 606/194 |
| 6,635,070 B2* | 10/2003 | Leeflang | A61B 17/22 | 606/200 |
| 6,652,505 B1* | 11/2003 | Tsugita | A61F 2/01 | 604/104 |
| 6,656,351 B2* | 12/2003 | Boyle | A61F 2/013 | 210/136 |
| 6,890,341 B2* | 5/2005 | Dieck | A61F 2/013 | 606/200 |
| 6,893,451 B2* | 5/2005 | Cano | A61F 2/013 | 606/127 |
| 6,932,831 B2* | 8/2005 | Forber | A61F 2/013 | 606/200 |
| 6,939,361 B1* | 9/2005 | Kleshinski | A61F 2/013 | 600/434 |
| 6,939,362 B2* | 9/2005 | Boyle | A61F 2/013 | 606/200 |
| 6,974,469 B2* | 12/2005 | Broome | A61B 17/221 | 606/200 |
| 7,235,061 B2* | 6/2007 | Tsugita | A61F 2/01 | 604/104 |
| 7,306,618 B2* | 12/2007 | Demond | A61F 2/01 | 604/164.05 |
| 7,481,823 B2* | 1/2009 | Broome | A61F 2/013 | 606/200 |
| 7,537,601 B2* | 5/2009 | Cano | A61F 2/013 | 606/200 |
| 7,691,122 B2* | 4/2010 | Dieck | A61F 2/013 | 606/198 |
| 7,763,044 B2* | 7/2010 | Inoue | A61F 2/01 | 606/200 |
| 7,862,578 B2* | 1/2011 | Tsugita | A61F 2/01 | 604/104 |
| 7,993,363 B2* | 8/2011 | Demond | A61F 2/01 | 604/164.05 |
| 8,231,651 B2* | 7/2012 | Tsugita | A61F 2/01 | 604/107 |
| 8,262,689 B2* | 9/2012 | Schneiderman | A61F 2/013 | 606/200 |
| 8,486,105 B2* | 7/2013 | Demond | A61F 2/01 | 604/164.05 |
| 8,702,747 B2* | 4/2014 | Honeycutt | A61F 2/01 | 606/200 |
| 9,011,479 B2* | 4/2015 | Koehler | A61F 2/01 | 606/200 |
| 9,271,818 B2* | 3/2016 | Urbanski | A61F 2/01 | |
| 2001/0025187 A1* | 9/2001 | Okada | A61F 2/01 | 606/200 |
| 2002/0022858 A1* | 2/2002 | Demond | A61F 2/01 | 606/200 |
| 2002/0055747 A1* | 5/2002 | Cano | A61F 2/013 | 606/108 |
| 2002/0072730 A1* | 6/2002 | McGill | A61F 2/013 | 604/525 |
| 2002/0082639 A1* | 6/2002 | Broome | A61B 17/221 | 606/200 |
| 2002/0121472 A1* | 9/2002 | Garner | A61F 2/013 | 210/348 |
| 2002/0161393 A1* | 10/2002 | Demond | A61F 2/01 | 606/200 |
| 2002/0173819 A1* | 11/2002 | Leeflang | A61B 17/22 | 606/200 |
| 2003/0004536 A1* | 1/2003 | Boylan | A61F 2/01 | 606/200 |
| 2003/0023264 A1* | 1/2003 | Dieck | A61F 2/013 | 606/200 |
| 2003/0023265 A1* | 1/2003 | Forber | A61F 2/013 | 606/200 |
| 2003/0042186 A1* | 3/2003 | Boyle | A61F 2/013 | 210/136 |
| 2003/0065354 A1* | 4/2003 | Boyle | A61F 2/013 | 606/200 |
| 2003/0065356 A1* | 4/2003 | Tsugita | A61F 2/01 | 606/200 |
| 2003/0100917 A1* | 5/2003 | Boyle | A61F 2/013 | 606/200 |
| 2003/0120303 A1* | 6/2003 | Boyle | A61F 2/013 | 606/200 |
| 2003/0144687 A1* | 7/2003 | Brady | A61F 2/01 | 606/200 |
| 2003/0144688 A1* | 7/2003 | Brady | A61F 2/01 | 606/200 |
| 2003/0153943 A1* | 8/2003 | Michael | A61F 2/013 | 606/200 |
| 2003/0171770 A1* | 9/2003 | Kusleika | A61F 2/013 | 606/200 |
| 2003/0208224 A1* | 11/2003 | Broome | A61F 2/013 | 606/200 |
| 2004/0006361 A1* | 1/2004 | Boyle | A61F 2/013 | 606/200 |
| 2004/0044360 A1* | 3/2004 | Lowe | A61F 2/013 | 606/200 |
| 2004/0059372 A1* | 3/2004 | Tsugita | A61F 2/01 | 606/200 |
| 2004/0082967 A1* | 4/2004 | Broome | A61F 2/013 | 606/200 |
| 2004/0087971 A1* | 5/2004 | Arnott | A61B 17/22031 | 606/127 |
| 2004/0093009 A1* | 5/2004 | Denison | A61F 2/013 | 606/200 |
| 2004/0093012 A1* | 5/2004 | Cully | A61F 2/013 | 606/200 |
| 2004/0098033 A1* | 5/2004 | Leeflang | A61B 17/22 | 606/200 |
| 2004/0138694 A1* | 7/2004 | Tran | A61F 2/01 | 606/200 |
| 2004/0153117 A1* | 8/2004 | Clubb | A61F 2/01 | 606/200 |
| 2004/0172055 A1* | 9/2004 | Huter | A61F 2/013 | 606/200 |
| 2004/0193208 A1* | 9/2004 | Talpade | A61F 2/013 | 606/200 |
| 2004/0199198 A1* | 10/2004 | Beulke | A61F 2/013 | 606/200 |
| 2004/0243173 A1 | 12/2004 | Inoue | | |
| 2004/0254601 A1* | 12/2004 | Eskuri | A61F 2/013 | 606/200 |
| 2005/0055048 A1* | 3/2005 | Dieck | A61F 2/013 | 606/200 |
| 2005/0075663 A1* | 4/2005 | Boyle | A61F 2/013 | 606/200 |
| 2005/0113862 A1* | 5/2005 | Besselink | A61F 2/013 | 606/200 |
| 2005/0159771 A1* | 7/2005 | Petersen | A61F 2/01 | 606/200 |
| 2005/0222583 A1* | 10/2005 | Cano | A61F 2/013 | 606/108 |
| 2006/0100659 A1* | 5/2006 | Dinh | A61F 2/013 | 606/200 |
| 2006/0229658 A1* | 10/2006 | Stivland | A61F 2/013 | 606/200 |
| 2006/0293705 A1* | 12/2006 | Neilan | A61F 2/013 | 606/200 |
| 2007/0118173 A1* | 5/2007 | Magnuson | A61F 2/013 | 606/200 |
| 2007/0219491 A1* | 9/2007 | Tsugita | A61F 2/01 | 604/104 |
| 2007/0233175 A1* | 10/2007 | Zaver | A61F 2/013 | 606/200 |
| 2007/0239198 A1* | 10/2007 | Brounstein | A61F 2/013 | 606/200 |
| 2007/0270900 A1* | 11/2007 | Renati | A61F 2/013 | 606/200 |
| 2007/0288054 A1* | 12/2007 | Tanaka | A61B 17/221 | 606/200 |
| 2008/0058860 A1* | 3/2008 | Demond | A61F 2/01 | 606/200 |
| 2008/0255596 A1* | 10/2008 | Jenson | A61B 17/221 | 606/159 |

(56) References Cited

U.S. PATENT DOCUMENTS

| | | | | |
|---|---|---|---|---|
| 2009/0062840 | A1* | 3/2009 | Angel | A61F 2/013 606/200 |
| 2009/0228036 | A1* | 9/2009 | Cano | A61F 2/013 606/200 |
| 2010/0152766 | A1* | 6/2010 | Dieck | A61F 2/013 606/200 |
| 2010/0191273 | A1* | 7/2010 | Keating | A61F 2/013 606/200 |
| 2011/0046656 | A1* | 2/2011 | Arnott | A61F 2/013 606/200 |
| 2011/0066177 | A1* | 3/2011 | Tsugita | A61F 2/01 606/200 |
| 2011/0230861 | A1 | 9/2011 | von Lehe et al. | |
| 2011/0264135 | A1* | 10/2011 | Demond | A61F 2/01 606/200 |
| 2013/0190803 | A1* | 7/2013 | Angel | A61B 5/0066 606/200 |
| 2014/0236220 | A1* | 8/2014 | Inoue | A61F 2/01 606/200 |

FOREIGN PATENT DOCUMENTS

| | | |
|---|---|---|
| JP | 2007518529 A | 7/2007 |
| JP | 2007325893 A | 12/2007 |
| WO | 03030740 A1 | 4/2003 |
| WO | 2004034884 A2 | 4/2004 |
| WO | 2005072648 A1 | 8/2005 |
| WO | 2006111943 A1 | 10/2006 |

OTHER PUBLICATIONS

ISA Japanese Patent Office, International Search Report of PCT/JP2012/074796, WIPO, Dec. 18, 2012, 6 pages.

State Intellectual Property Office of the People's Republic of China, Office Action Issued in Chinese Patent Application No. 201280046950.7, Aug. 24, 2015, 5 pages.

Japan Patent Office, Notice of Allowance Issued in Patent Application No. 2013-536369, Jun. 30, 2016, 3 pages.

* cited by examiner

DEVICE FOR CAPTURING DEBRIS IN BLOOD VESSELS

TECHNICAL FIELD

The present invention relates to a device for capturing debris in a blood vessel, which is inserted into a blood vessel to capture debris such as a thrombus, and prevents the thrombus and the like from flowing to a downstream side of the device.

BACKGROUND ART

In the past, as this sort of debris capturing device, for example, one as disclosed in Patent Literature 1 has been known. The debris capturing device 100' is one that is, as illustrated in FIG. 43, adapted such that a filter member 3' is attached to a fore end part of a wire 2' inserted into a blood vessel, and for example, by arranging the filter member 3' in a blood vessel during a medical operation or an operation for endovascular treatment, prevents a thrombus or the like detached during the operation from flowing toward a downstream side of the filter member 3'.

The filter member 3' includes: a baglike filter 32' formed of mesh fabric; and a ringlike elastic steel wire 31' attached around an opening edge of the filter 32'. The filter 32' can pass blood components such as blood cells and blood platelets and captures a thrombus and the like larger than such blood components, and in the blood vessel, the ringlike elastic steel wire 31' is spread and arranged so as to make an opening of the filter 32' orthogonal to blood flow.

The filter member 3' is attached to the wire 2' with four threads 4'. Each of the threads 4' is, at one end part thereof, attached to a predetermined position of the wire, and at the other end part thereof, attached to a corresponding one of four positions of the ringlike elastic steel wire 31'. Also, in a state where the ringlike elastic steel wire 31' is spread and formed in a circular shape, the threads 4' are, as illustrated in FIG. 43, like parachute strings, formed in a conical configuration that spreads toward a downstream side of the blood flow as a whole.

Next, an example of the use of the debris capturing device 100' in the case of, for example, relieving a stenosis in a carotid artery is briefly described.

First, a tubular body 1' as illustrated in FIG. 44 is inserted into the blood vessel to position a fore end thereof at a base part of the carotid artery, i.e., at a site where the carotid artery branches from an aorta.

Then, a filter conveyance tube 12' referred to as a conveyance sheath is protruded from the fore end of the tubular body 1' through the inside of the tubular body 1', and sent out until a fore end of the filter conveyance tube 12' passes through a target stenosis part and is positioned at a periphery of the stenosis part. The filter member 3' attached to the wire 2' is stored in a fore end part of the filter conveyance tube 12'.

Subsequently, by pulling back only the filter conveyance tube 12' while leaving the wire 2' unmoved, the filter member 3' is released from the filter conveyance tube 12'.

In doing so, the ringlike elastic steel wire 31' is spread by an elastic restoring force thereof, and as illustrated in FIG. 43, the opening of the filter 32' is arranged orthogonally to blood flow on a peripheral side of the stenosis part.

Then, after the filter conveyance tube 12' has been pulled out of the body, a balloon catheter, a stent, or the like is conveyed to the stenosis part along the wire 12' to perform treatment.

After that, when recovering the filter member 3', an operation tube 13' having at least a smaller fore end part than that of the filter conveyance tube 12' is sent out along the wire 2' to pull the respective threads 4' into the operation tube 13'.

In doing so, the other end parts of the respective threads 4', i.e., sites at which the respective threads 4' are attached to the ringlike elastic steel wire 31' are brought close to one another toward an opening of the operation tube 13', and a contraction force acts on the ringlike elastic steel wire 31'.

As a result, as illustrated in FIG. 45, the ringlike elastic steel wire 31' starts to bend alternately convexly and concavely at intermediate sites between the four points attached to the respective threads 4'.

Finally, the other end parts of the respective threads 4' are gathered in a fore end opening part of the operation tube 13', and as illustrated in FIG. 46, the ringlike elastic steel wire 31' is folded into a substantially rodlike shape along an extending direction of the wire 2' as a whole.

At this time, as illustrated in FIG. 46, parts of the ringlike elastic steel wire 31' hold the fore end part of the operation tube 13' from radially outside.

After that, as illustrated in FIGS. 46 and 47, the filter member 3' is recovered by, while staying in a state where the folded filter member 3' is attached to the fore end part, pulling the operation tube 13' into the tubular body 1' and pulling out the operation tube 13'.

CITATION LIST

Patent Literature

Patent Literature 1
Re-publication of PCT International Publication No. 03/030740

SUMMARY OF INVENTION

Technical Problem

However, in the above-described filter member 3', holding parts K where the fore end part of the operation tube 13' is held from outside may be, as illustrated in FIG. 48, slightly separated from an outer circumferential surface of the operation tube 13'. This may occur in the case where the wire 2' is not sufficiently pulled into the operation tube 13', or the holding parts K face outward due to some cause.

In the case of recovering the filter member 3' in such a state, if the operation tube 13' is deviated in any direction toward the tubular body 1', as illustrated in FIG. 49, when the filter member 3' attached to the fore end part of the operation tube 13' fits in from a fore end opening of the tubular body 1', any of the holding parts K may be caught by an opening edge of the tubular body 1' to make storage difficult.

On the other hand, in the case of, in order to eliminate the catch, employing a complicated structure, a medical operation may be adversely influenced because the complicated structure makes an operation difficult or causes damage or trouble.

The present invention is made in consideration of such a problem, and a man object thereof is to provide a device for capturing debris in blood vessels, which enables a filter member to be smoothly recovered, and has a simple structure leading to an easy operation.

Solution to Problem

That is, the device for capturing debris in blood vessels according to the present invention is provided with:

a core wire that is arranged in a blood vessel;

a filter member that includes a baglike filter arranged in the blood vessel such that an opening faces to an upstream side of blood flow, and a ringlike elastic wire rod attached around an opening edge part of the filter to be, in a spread state, formed in an annular shape spread by an elastic restoring force thereof, and can be brought into two states, i.e., a folded state of being attached to a fore end part of the core wire and recoverable and the spread state of being spread in the blood vessel;

a plurality of linear bodies of which one end parts are respectively attached to a plurality of positions of the ringlike elastic wire rod and the other end parts are attached on a base side of the core wire with respect to the one end parts, the plurality of linear bodies connecting the filter member to the core wire;

a slide tube inside which the core wire passes; and an actuator member that moves the slide tube along the core wire, and configured such that, in a case of moving the slide tube toward a fore end side of the core wire with the actuator member from the spread state to thereby pull the linear bodies into the slide tube from the other end parts of the linear bodies, the one end parts of the respective linear bodies and the plurality of positions of the ringlike elastic wire rod come close to each other, the plurality of positions being respectively attached to the one end parts, and the ringlike elastic wire rod is bent so as to hold a fore end part outer circumferential surface of the slide tube from radially outside, and brought into the folded state.

Also, the device for capturing debris in blood vessel is characterized by being provided with a guide member having a guide surface that, in the folded state, extends in a direction toward a base from a fore end part of a holding part in the ringlike elastic wire rod toward an outer circumferential surface of the slide tube.

If so, at the time of pulling the filter member holding the slide tube into a tubular body such as a catheter to recover the filter member, even in the case where the fore end part of the holding part is separated from the fore end part outer circumferential surface of the slide tube, the guide member is present between them, and therefore a fore end opening edge of the tubular body can be prevented from fitting in. Accordingly, the filter member can be smoothly recovered without being caught by the tubular body or the like.

As the actuator member, an operation tube that is arranged on a base side of the slide tube and guided by the core wire to move forward and backward can be used. Preferably, the core wire passes through at least a fore end part of the operation tube, and is configured to press the slide tube with a fore end of the operation tube to move the slide tube toward the fore end side of the core wire in such a way that an operator operates the operation tube so as to relatively move the operation tube toward the fore end side of the core wire.

As a specific embodiment of the guide member, a guide member formed of an elastic steel wire having predetermined flexural rigidity can be used.

Specific embodiments for, during a period from the spread state to the folded state, surely preventing the elastic steel wire from being significantly loosened to fail in fulfilling a function of the elastic steel wire can include one in which the elastic steel wire is, at a base end part thereof, attached to the core wire, from the base end part, passes between the slide tube and the operation tube or through a steel wire throughhole provided in a lateral circumferential wall of the slide tube to extend toward the fore end part of the holding part, and is slidably attached to the fore end part of the holding part along an extending direction of the core wire. Note that "along an extending direction of the core wire" means "along a direction including a component of a direction in which the core wire extends."

In terms of preventing from catching at the time of recovery, it is preferable that the elastic steel wire is attached to a radial outside of the fore end part of the holding part.

In the case where the ringlike elastic wire rod forms a pair of opposite holding parts in the folded state, wherein a pair of elastic steel wires provided correspondingly to the respective holding parts is configured to extend inside the filter from fore end parts of the respective holding parts, and integrally connect to each other to form a loop shape, fabrication becomes very easy. This is because it is only necessary to, with use of the substantially one elastic steel wire, attach both end parts thereof to the core wire to form the elastic steel wire in the loop shape, and attach opposite parts thereof to the ringlike elastic wire rod. Also, in the spread state, the elastic steel wire fits into the filter to play a role in spreading the filter, and therefore a shape of the filter in the blood vessel can be preferably kept.

In order to more surely arrange the filter member in the blood vessel in a posture where an opening of the filter member is substantially orthogonal to a blood flow direction, desirably, the device for capturing debris in blood vessel is further provided with a plurality of second linear bodies of which one end parts are respectively attached to a plurality of positions of the ringlike elastic wire rod and the other end parts are attached on the fore end side of the core wire with respect to the one end parts, wherein the plurality of second linear bodies connect the ringlike elastic wire rod to the core wire.

In the case where the ringlike elastic wire rod is configured by winding a thin steel wire, any end parts tends to be radially exposed and may catch on a blood vessel, tubular body, thin tube, or the like. In order to reasonably resolve this, it is preferable that both end excess parts of the thin steel wire are extended inside the filter and attached to the core wire so as to lie along the core wire.

In the case where the core wire is one including a fore end core wire attached to the filter member, and a base core wire on a base side with respect to the fore end core wire, and configured to be able to bring or separate the fore end core wire and the base core wire into contact with or from each other, the option of, during a medical operation, leaving the filter member in the blood vessel becomes possible, and therefore an artificial blood vessel operation or the like is facilitated.

Also, preferably, as the base core wire, two types are provided, i.e., a conveyance core wire used at a time of placing the filter member in the blood vessel and a recovery core wire used at a time of recovering the filter member from the blood vessel, wherein a fore end part of the conveyance core wire is provided with a pressing surface that presses an engaged part provided in a base end part of the fore end core wire without engaging with the engaged part, and a fore end part of the recovery core wire is provided with an engaging part that engages with the engaged part.

In the case where the engaged part is a hook part that is formed by bending the base end part of the core wire in the fore end core wire toward the fore end side, and the engaging part is a ring part that is provided at the fore end part of the core wire in the base core wire to engage with the engaged part, wherein a bent end part of the hook part is further bent to form a burr part, the ring part once caught can be preferably prevented from being removed by a further operation from the caught state.

Further, in the case where the hook part is configured to, at the time of placing the filter member in the blood vessel, spread an angle formed with the fore end core wire by an elastic restoring force thereof, the bend angle spreads when the filter member is released into the blood vessel, and therefore capturing is facilitated. On the other hand, at the time of conveyance, or capturing and storage, the bend angle decreases, and therefore even in the case of making the operation tube and the like thin, the hook part that was spread larger than a diameter of the operation tube can be reasonably stored.

Also, the device for capturing debris in blood vessels according to the present invention is provided with:

a core wire that is arranged in a blood vessel;

a filter member that includes a baglike filter arranged in the blood vessel such that an opening faces an upstream side of blood flow, and a ringlike elastic wire rod attached around an opening edge part of the filter to be, in a spread state, formed in an annular shape spread by an elastic restoring force thereof, can be brought into two states, i.e., a folded state of being recoverable and the spread state of being spread in the blood vessel, and is attached to a fore end part of the core wire; and an elastic steel wire that is, in a natural state, formed in an annular shape spread by an elastic restoring force thereof, wherein one position thereof on a base end side is attached to the core wire, and opposite positions on a fore end side with respect to the position of the attachment to the core wire are respectively attached to opposite positions of the ringlike elastic wire rod, wherein the elastic steel wire is configured to: be able to converge along the core wire to thereby deform the filter member from the spread state to the folded state; in the spread state, with substantially orthogonally or obliquely intersecting with the ringlike elastic wire rod, annularly spread; and position a fore end side with respect to the opposite positions inside the filter.

If so, the filter member is connected to the core wire only with the elastic steel wire, and therefore a configuration is extremely simple. Also, the holding part that holds the outer circumferential surface of the slide tube at the time of folding is not present, and therefore the filter member can be smoothly recovered without catching.

Further, the elastic steel wire is formed in the loop shape, and partially fits inside the filter member, so that in the spread state, the elastic steel wire plays a role in spreading the filter member, and the filter member can be surely arranged in the blood vessel in a preferable state.

More specifically, the device for capturing debris in blood vessel further provided with a tube member that is provided so as to be movable forward and backward along the core wire by passage of the core wire through an inside of the tube member, and configured such that in a case where from the spread state, the core wire is relatively moved toward the inside of the tube member to pull the elastic steel wire into the tube member until the opposite positions of the elastic steel wire are positioned at a fore end of the tube member, as the opposite positions of the elastic steel wire are brought close to each other, the opposite positions of the ringlike elastic wire rod are brought into a state of being close to each other, and in a case where further from the state, they are relatively moved such that the core wire is pulled into the tube member, the ringlike elastic wire rod is brought into the folded state of being bent at the respective opposite positions so as to lie along the core wire, and part or all of the ringlike elastic wire rod is stored in the tube member can be used.

The tube member may be configured to include an inner operation tube element and an outer operation tube element, wherein the core wire passes through an inside of the inner operation tube element, and the device for capturing debris in blood vessel may be configured such that in a case where from the spread state, the core wire is relatively moved toward the inside of the inner operation tube element to pull the elastic steel wire into the inner operation tube element until the opposite positions of the elastic steel wire are positioned at a fore end of the inner operation tube element, as the opposite positions of the elastic steel wire are brought close to each other, the opposite positions of the ringlike elastic wire rod are brought into a state of being close to each other, and in a case where further from the state, the outer operation tube element is sent out relatively to the inner operation tube element and the core wire, the ringlike elastic wire rod is brought into the folded state of being bent at the respective opposite positions so as to lie along the core wire, and part or all of the ringlike elastic wire rod is stored in the outer operation tube element.

If so, at least a fore end part of the inner operation tube element can be made thin to form a figure eight shape in which the opposite positions of the ringlike elastic wire rod are in closer contact with each other, and therefore it is possible to form a smaller folded shape. On the other hand, a fore end part of the inner operation tube element is thin, and in such a state, it is impossible to pull the ringlike elastic wire rod into the inner operation tube element to bend the ringlike elastic wire rod; however, in the state where the ringlike elastic wire rod is formed in the figure eight shape, by sending out the outer operation tube element preliminarily inserted with the inner operation tube element, the ringlike elastic wire rod can be bent with the outer operation tube element, and then recovered inside the outer operation tube element while folded.

Advantageous Effects of Invention

According to the present invention configured as described, even in the case where when at the time of recovering the filter member, the filter member fits into the tubular body from the fore end opening of the tubular body, the fore end of the holding part is slightly separated from the outer circumferential surface of the slide tube, the guide member is present between the fore end and the outer circumferential surface to play a role in sliding at the opening edge of the tubular body, and therefore the fore end opening edge of the tubular body does not fit in the gap between the outer circumferential surface of the slide tube and the holding part. Accordingly, without the holding parts being caught by the opening edge of the tubular body, the filter member can be smoothly pulled into the tubular body.

In addition, the configuration is extremely simple because only the elastic steel wire is provided.

REFERENCE CHARACTER LIST

Figure 1:
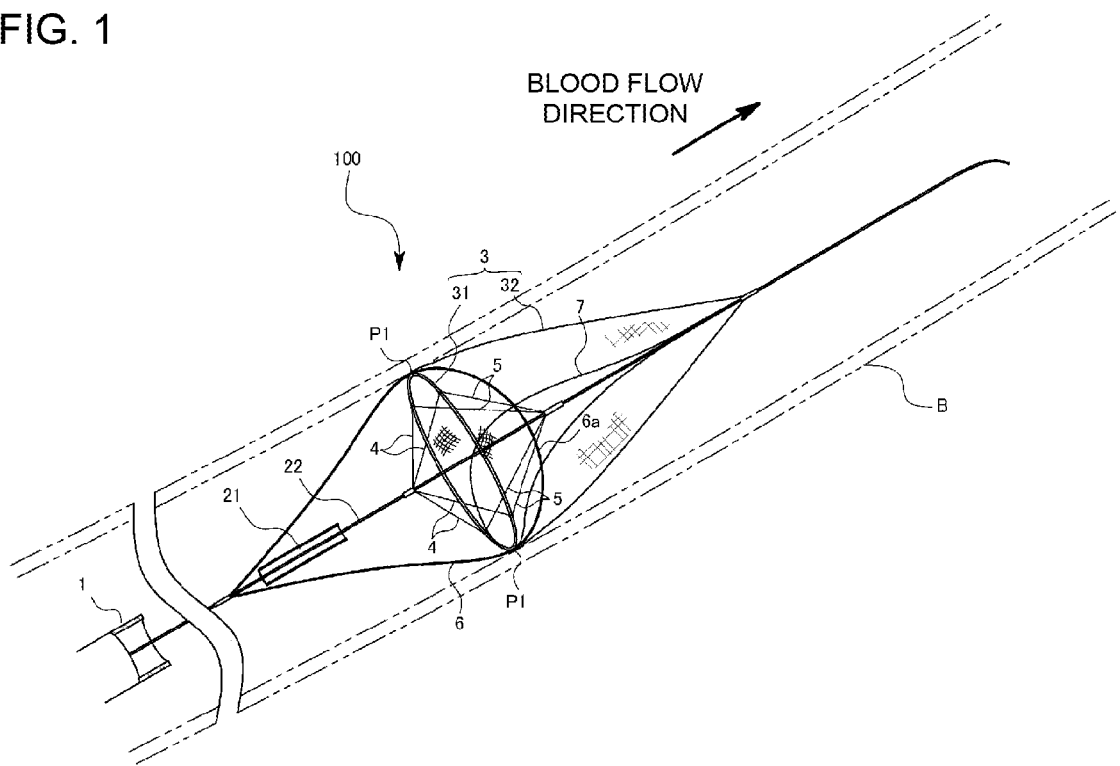
FIG. 1 is an overall perspective view illustrating a spread state at the time of placing a device for capturing debris in blood vessels in a first embodiment of the present invention (illustrating internal structure while partially exploded).

100 Device for capturing debris in blood vessels
1 Tubular body
13 Operation tube
21 Slide tube
22 Core wire (wire)
3 Filter member
31 Ringlike elastic wire rod
32 Filter
6 Guide member (elastic steel wire)

DESCRIPTION OF EMBODIMENTS

First Embodiment

A device 100 for capturing debris in blood vessels of a first embodiment is one that is, as illustrated in FIG. 1, provided with: a wire 22 as a core wire that passes through the inside of a tubular body 1 inserted into a blood vessel B; and a filter member 3 that is attached to a fore end part of the wire 22, and by arranging the filter member 3 in the blood vessel B during, for example, a medical operation, with the filter member 3, captures a thrombus or the like detached by the medical operation to prevent the thrombus or the like from flowing toward a downstream side of the filter member 3.

The respective parts are described.

The tubular body 1 is one that is referred to as a catheter, and formed with use of a hollow and soft material having a predetermined torque transmissibility. The tubular body 1 is inserted into the blood vessel B from outside the body through the skin, and arranged such that, for example, a fore end thereof comes close to a position to place the filter member 3.

The wire 22 is one that has a predetermined flexural rigidity and torque transmissibility and is made of steel.

Figure 2:
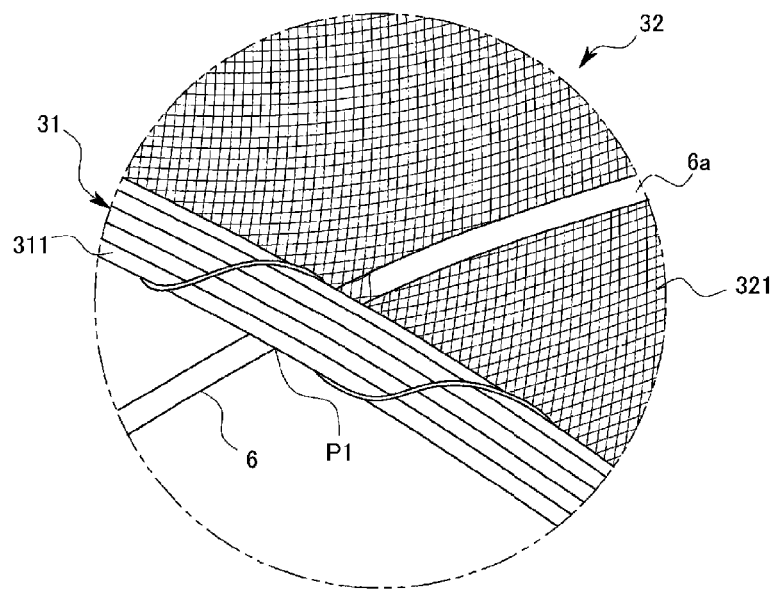
FIG. 2 is a partially enlarged view illustrating a part of attachment of an elastic steel wire to a ringlike elastic wire rod in the same embodiment (as viewed from the inside of a filter).

The filter member 3 is one that is, as illustrated in FIGS. 1 and 2, and other drawings, arranged such that an opening thereof is positioned on a base end side, i.e., on an upstream side of blood flow, and provided with: a baglike filter 32 of which a bottom part positioned on a downstream side of the blood flow has a narrowed shape; and a ringlike elastic wire rod 31 that is attached around an opening edge of the filter 32.

The filter 32 is formed by weaving fine resin thread 321 in the form of mesh, and on a surface of the resin thread 321, a special coating to which blood components are unlikely to attach is applied. On the basis of such a configuration, the filter 32 has characteristics capable of making clogging unlikely to occur, and being arranged in the blood vessel B for a period of time several tens of times longer as compared with an existing filter. Note that as illustrated in FIG. 2, the filter 32 is configured to make a direction of the mesh oblique to the opening edge of the filter 32.

Figure 3:
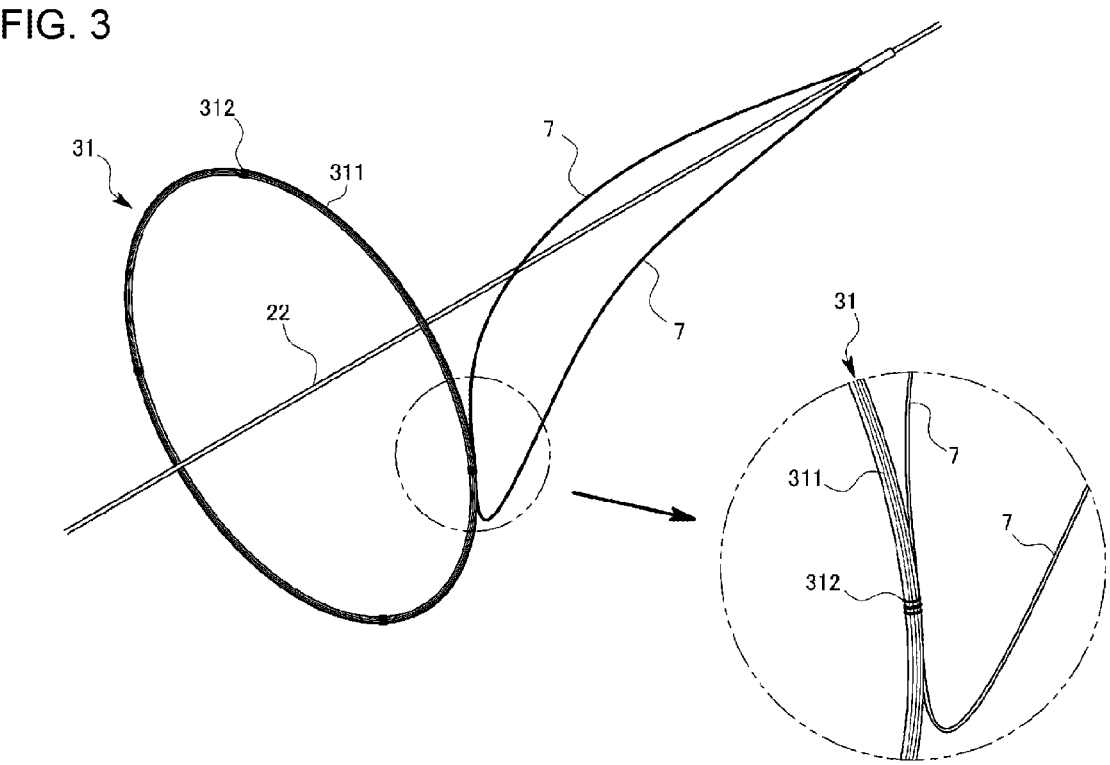
FIG. 3 is a perspective view illustrating the ringlike elastic wire rod and excess parts in the same embodiment.

The ringlike elastic wire rod 31 is one that is, as illustrated in FIGS. 2 and 3, configured by multiply winding a fine steel wire 311 and bundling the multiply wound wire at a plurality of positions with threads 312 or the like, and in a natural state where external force does not act, formed in an annular shape by an elastic restoring force thereof to fulfill a function of spreading the opening of the filter 32. Note that in this embodiment, excess parts 7 of the wound fine steel wire 311 (hereinafter referred to as excess parts 7) are spirally extended into the filter 32, and fore end parts of the excess parts 7 are sewed or bonded to the wire 22 so as to lie along the wire 22.

Such a filter member 3 is attached to the wire 22 through a plurality of (four in this embodiment) linear bodies 4. The linear bodies 4 are ones that are respectively formed of fine resin threads having an extremely small flexural rigidity, and one end parts thereof are attached to positions at which the ringlike elastic wire rod 31 is substantially divided into four sections. Also, the other end parts are fastened while bundled on a base end side of the wire 22 with respect to the one end parts. Further, in a spread state where the ringlike elastic wire rod 31 is spread and formed in the annular shape, the one end parts of the linear bodies 4 are positioned on the downstream side of the blood flow with respect to the other end parts, and as illustrated in FIG. 1, the linear bodies 4 are configured to form a conical shape that spreads toward the downstream side of the blood flow as a whole.

Also, in locations opposite to those of the linear bodies 4 with respect to the ringlike elastic wire rod 31, four second linear bodies 5 are provided, of which one end parts are attached to four positions (in this embodiment, the same positions as the attachment positions of the linear bodies 4) of the ringlike elastic wire rod 31, and the other end parts are attached on a fore end side of the wire 22 with respect to the one end parts. The second linear bodies 5 are configured to, in the spread state where the ringlike elastic wire rod 31 is spread and formed in the annular shape, as illustrated in FIG. 1, form a conical shape that spreads out toward the upstream side of the blood flow as a whole.

In addition, in this embodiment, by attaching an intermediate part of one threadlike body to the ringlike elastic wire rod 31 and fixing both ends of the threadlike body to base and fore end sides of the core wire, one of the linear bodies 4 and a corresponding one of the second linear bodies 5 are formed of an integrated member (the threadlike body). This is to facilitate the simplification of fabrication. Accordingly, the positions of the attachment to the ringlike elastic wire rod 31 are the same between the linear bodies 4 and corresponding ones of the second linear bodies 5.

Further, in the spread state, the filter member 3 is kept by the linear bodies 4 and second linear bodies 5 in a posture where an opening face thereof is substantially orthogonal to the wire 22, i.e., substantially orthogonal to a blood flow direction. Note that the wire 22 in this embodiment is configured to slidably penetrate through the bottom part of the filter 32 and make a fore end thereof protrude from the filter 32 by a predetermined length. In addition, in order to make the wire 22 slidable, the wire 22 may be made to penetrate through a mesh in the bottom part of the filter 32, or an unillustrated tube into which the wire 22 is inserted may be provided and attached to the bottom part of the filter 32.

Still further, this embodiment is, as illustrated in FIG. 1, configured to, on the base side with respect to the linear bodies 4, fit a tubular slide tube 21 having a predetermined length at the outside of the wire 22, and by sewing or bonding, fix both end parts of one elastic steel wire 6 having a predetermined flexural rigidity to the base side of the wire 22 with respect to slide tube 21 to make the elastic steel wire 6 have a loop shape that passes outside the slide tube 21 toward the fore end side of the wire 22.

Two opposite positions P1 of the loop-shaped elastic steel wire 6 are respectively attached to opposite positions of the ringlike elastic wire rod 31, and specifically, to intermediate positions between the attachment positions of the linear bodies 4, and the present embodiment is configured to, in the spread state, make the elastic steel wire 6 and the ringlike elastic wire rod 31 substantially orthogonal to each other at the mutual attachment positions P1.

Figure 4:
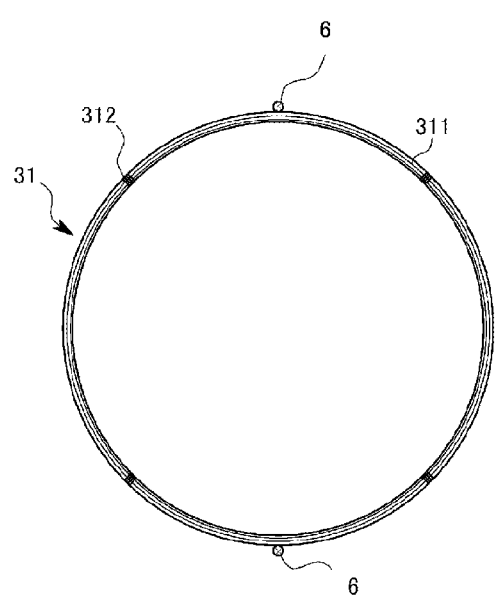
FIG. 4 is a diagram illustrating a positional relationship between the elastic steel wire and the ringlike elastic wire rod as viewed from an axial direction in the same embodiment.

Also, at the attachment positions P1, the elastic steel wire 6 is structured to be slidable along an extending direction of the wire 22 with respect to the ringlike elastic wire rod 31. More specifically, at the attachment positions P1, as illustrated in FIGS. 2 and 4, the elastic steel wire 6 is adapted to pass radially outside the ringlike elastic wire rod 31 and penetrate through a mesh of the filter 32 near the passage point, and the mesh of the filter 32 slidably connects the ringlike elastic wire rod 31 and the elastic steel wire 6 to each other. Note that a configuration to make them slidable with respect to each other is not limited to this, and for example, the present invention may be adapted to attach a thread to the ringlike elastic wire rod to form a ring with the thread, and pass the elastic steel wire through the ring.

Next, an operating method related to placement, recovery, and the like of the device 100 for capturing debris in blood vessels having such a configuration is described with reference to FIG. 5 and other drawings.

First, the tubular body 1 is inserted into the blood vessel B from the same direction as the blood flow direction, and the fore end thereof is arranged on an upstream side of a site to place the filter member 3. A position to place the filter member 3 is on a downstream side of a blood vessel site (e.g., a stenosis part) to be treated. In addition, a method for inserting the tubular body 1 into the blood vessel B, and the like are already known, and therefore description thereof is omitted here.

Figure 5:
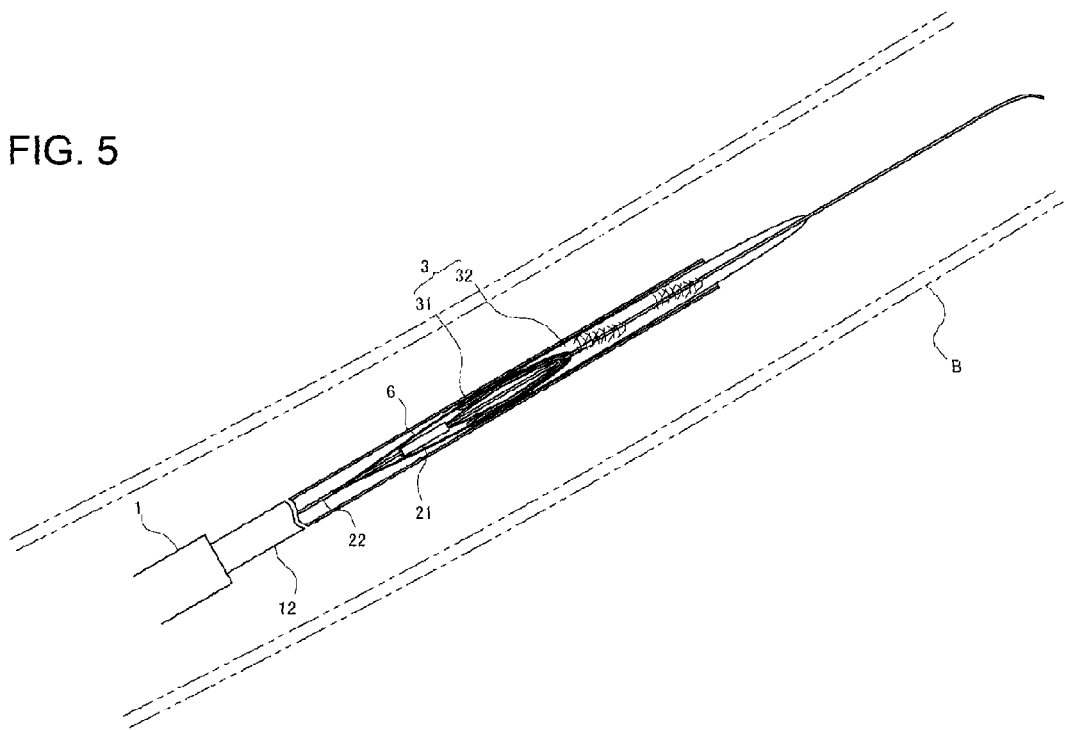
FIG. 5 is a conveyance state diagram of a filter member in the same embodiment.
Figure 6:
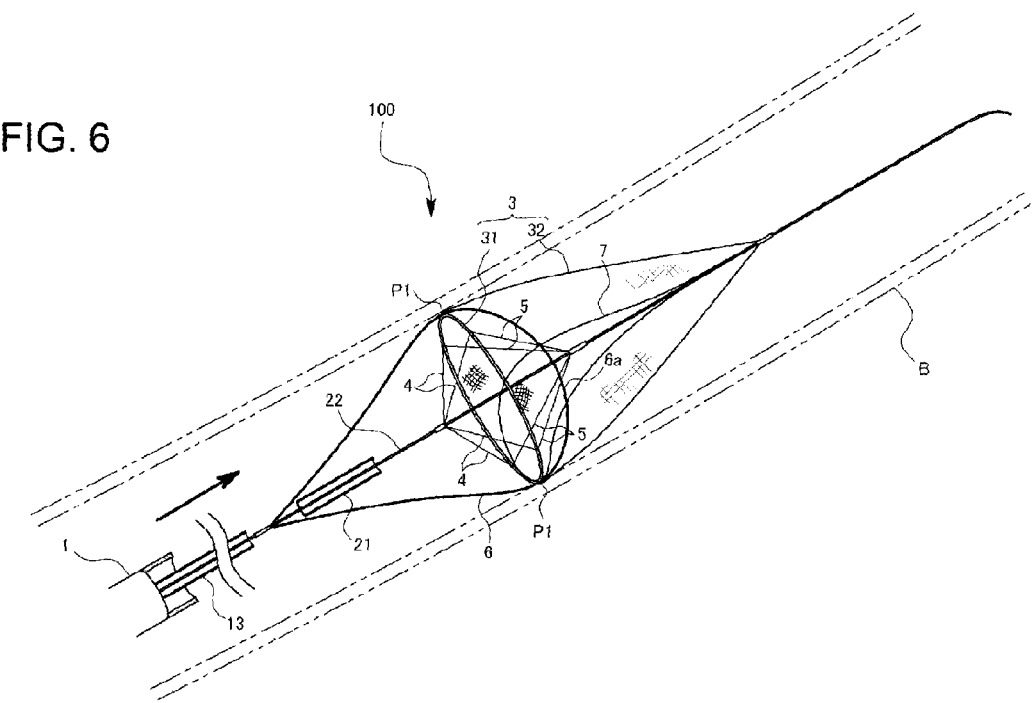
FIG. 6 is a recovery start state diagram of the filter member in the same embodiment.

Subsequently, a filter conveyance tube 12 referred to as a conveyance sheath is, as illustrated in FIG. 5, passed through the inside of the tubular body 1 and protruded from the fore end of the tubular body 1, and sent out until a fore end of the filter conveyance tube 12 passes the target stenosis part and is positioned at a periphery of the stenosis part. In the fore end part of the filter conveyance tube 12, the filter member 3 attached to the wire 22, and the like, are stored.

Then, without moving the wire 22, the filter conveyance tube 12 is pulled out, and the filter member 3 is taken out of the fore end of the filter conveyance tube 12. In doing so, the ringlike elastic wire rod 31 is annularly spread in the blood vessel B, and the opening of the filter member 3 is also spread. On the other hand, a posture binding force caused by the linear bodies 4 and second linear bodies 5 acts on the ringlike elastic wire rod 31, and finally, as illustrated in FIG. 1, the filter 32 is annularly spread so as to make the opening thereof orthogonal to the blood flow direction, and the opening comes into close contact with an inner circumferential wall of the blood vessel B.

At this time, the elastic steel wire 6 is formed in the loop shape orthogonal to the ringlike elastic wire rod 31, and a fore end part 6a thereof is positioned inside the filter 32.

The filter member 3 is placed in this manner.

In the case of recovering the filter member 3, an operation tube 13 having at least a smaller diameter fore end part than a fore end part of the filter conveyance tube 12 is sent out while fitted at the outside of the wire 22. Note that regarding the operation tube 13, only the fore end part thereof may be fitted at the outside of the wire 22. Further, regarding the operation tube 13, at least the fore end part thereof has substantially the same diameter as that of the slide tube 21, and has a smaller diameter than that of the filter conveyance tube 12.

This causes the slide tube 21 to be pressed by the fore end of the operation tube 13 to move toward the linear body 4 side, and the linear bodies 4 are started to be pulled into the slide tube 21. Then, correspondingly to this, the one end parts of the respective linear bodies 4, i.e., the respective sites attached to the ringlike elastic wire rod 31, come close to one another toward a fore end opening of the slide tube 21, and a contraction force acts on the ringlike elastic wire rod 31.

Figure 7:
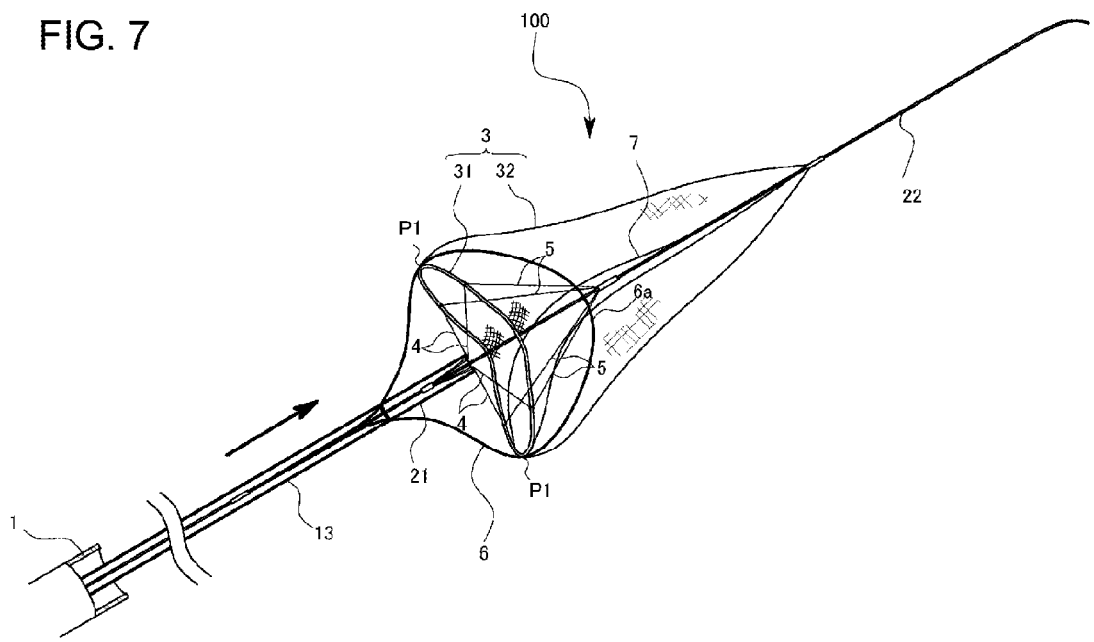
FIG. 7 is a recovery halfway state diagram of the filter member in the same embodiment.

As a result, as illustrated in FIG. 7, the ringlike elastic wire rod 31 starts to bend alternately convexly and concavely at intermediate sites between the four positions attached to the respective linear bodies 4. The reason why the ringlike elastic wire rod 31 bends without the convexity and concavity being reversed is because in a first storage state of the filter conveyance tube 12, the ringlike elastic wire rod 31 is bent at the sites, and made to have a tendency to easily bend.

After that, the other end parts of the respective linear bodies 4 are gathered in the fore end opening part of the slide tube 21, and the ringlike elastic wire rod 31 is folded into a substantially rodlike shape along the extending direction of the wire 22 as a whole.

Figure 8:
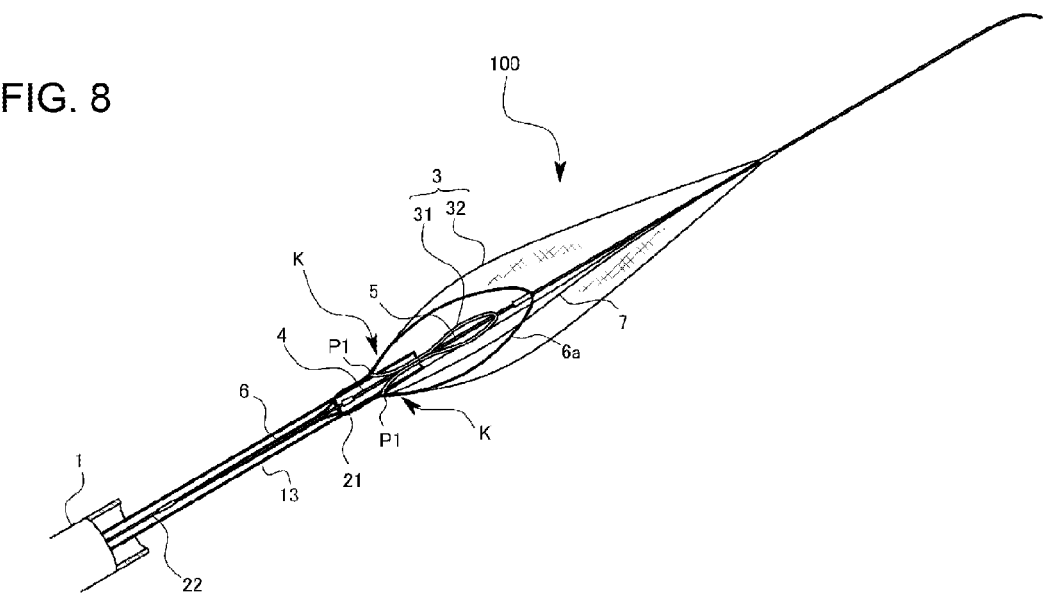
FIG. 8 is a recovery halfway state diagram of the filter member in the same embodiment.
Figure 9:
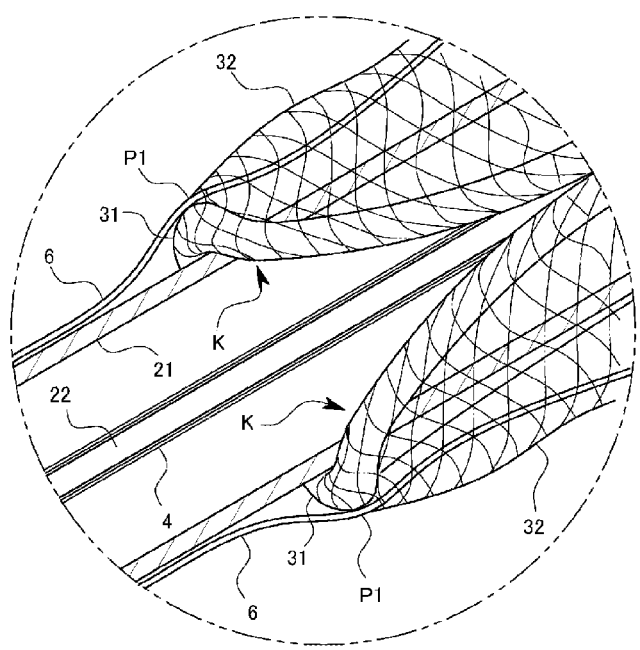
FIG. 9 is a partially enlarged perspective view illustrating holding parts in the same embodiment.

At this time, as illustrated in FIGS. 8 and 9, parts of the ringlike elastic wire rod 31 hold the fore end part of the slide tube 21 from radially outside.

On the other hand, the elastic steel wire 6 is, as illustrated in FIG. 7, as the ringlike elastic wire rod 31 is bent, brought into a twofold state of being bent at the fore end part thereof while sliding at the positions of the attachment to the ringlike elastic wire rod 31.

At this time, as illustrated in FIGS. 8 and 9, the elastic steel wire 6 passes outside holding part fore ends P1 in the ringlike elastic wire rod 31 to extend outside the slide tube 21 along an extending direction of the slide tube 21, and is brought into a state of being fitted into the operation tube 13 from between the slide tube 21 and the operation tube 13.

Figure 10:
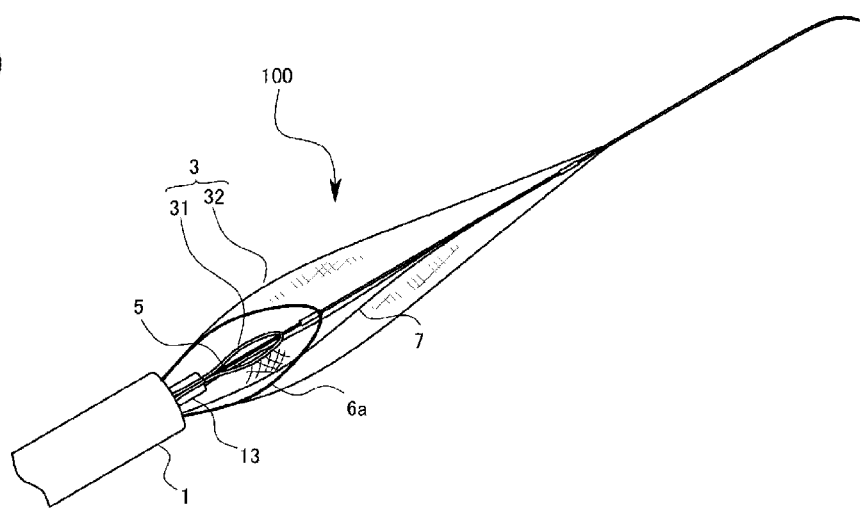
FIG. 10 is a recovery halfway state diagram of the filter member in the same embodiment.

Finally, the wire 22 is moved back with a state where the fore end thereof is attached to the folded filter member 3 being kept, and through a state in FIG. 10, pulled out through the inside of the tubular body 1 to recover the filter member 3.

Figure 11:
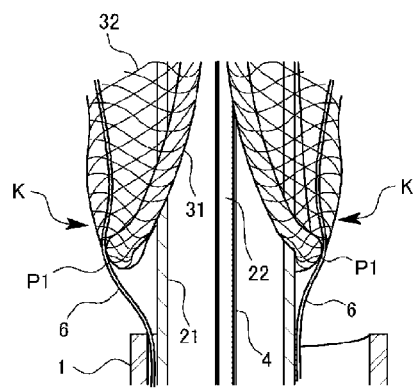
FIG. 11 is a partially enlarged view illustrating the holding parts of the filter member in the process of recovery in the same embodiment.
Figure 12:
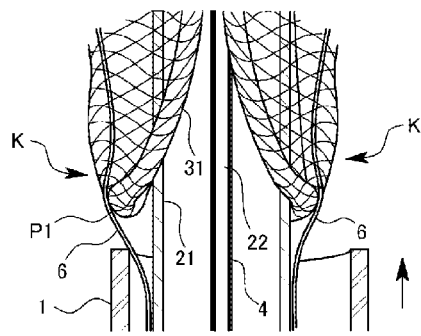
FIG. 12 is a partially enlarged view illustrating the holding parts of the filter member in the process of recovery in the same embodiment.
Figure 13:
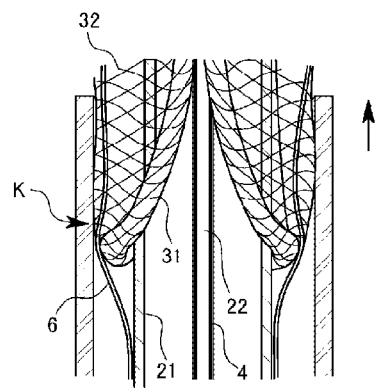
FIG. 13 is a partially enlarged view illustrating the holding parts of the filter member in the process of recovery in the same embodiment.

Accordingly, even in the case where at the time of recovering the filter member 3, the filter member 3 fits inside the tubular body 1 from the fore end opening of the tubular body 1, the operation tube 13 is displaced from the centerline of the tubular body 1, and any of the fore ends P1 of the holding parts K is slightly separated from an outer circumferential surface of the slide tube 21. In the case of such a configuration, as illustrated in FIG. 11, the elastic steel wire 6 having the predetermined flexural rigidity is bridged between them, so that an outer circumferential surface of the elastic steel wire 6 acts as a guide surface, and therefore the elastic steel wire 6 plays a role as a guide member that enables sliding at an opening edge of the tubular body 1. Specifically, as illustrated in FIGS. 12 and 13, the tubular body 1 stores the filter member 3 with an inner circumferential surface of the fore end opening edge of the tubular body 1 moving along the outer circumferential surface of the elastic steel wire 6 not only in an axial direction but also in a radial direction, and therefore fitting in any of gaps between the outer circumferential surface of the slide tube 21 and the holding parts K does not occur. That is, without any of the holding parts K being caught by the opening edge of the tubular body 1, the filter member 3 can be smoothly pulled into the tubular body 1 with the elastic steel wire 6 as a guide.

In addition, the configuration is extremely simple because only the elastic steel wire 6 is provided.

Besides, the following effects can also be mentioned.

The elastic steel wire 6 is formed in the loop shape, and as illustrated in FIG. 1, the fore end part 6a thereof fits inside the filter 32, so that in the spread state, the elastic steel wire 6 plays a role in spreading the filter 32, and therefore the filter 32 can be arranged in the blood vessel B in a state where the inside thereof expands, which is suitable for capturing a thrombus or the like.

Figure 26:
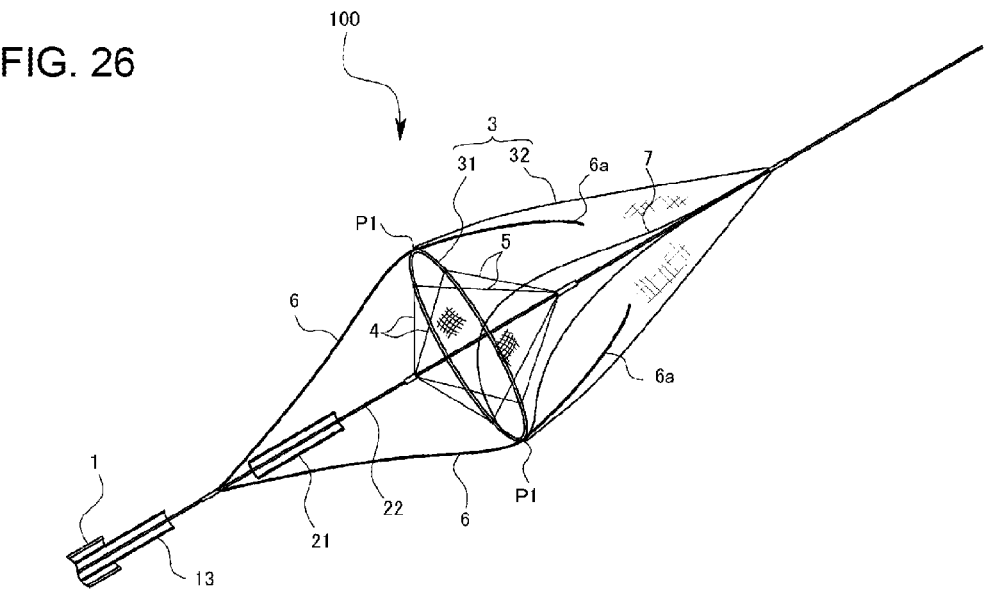
FIG. 26 is a perspective view illustrating a device for capturing debris in blood vessel in another further variation of the same embodiment.

The elastic steel wire 6 is formed in the loop shape, and both end parts thereof are fastened to the wire 22 so as to lie along the wire 22, so that end part treatment is extremely easy. In the present invention, as will be described later, the elastic steel wire 6 is not necessarily formed in the loop shape, and as illustrated in FIG. 26, theoretically, a pair of elastic steel wires 6 may be provided; however, in such a case, the end part (fore end part) treatment becomes a problem, and as compared with this case, the above-described effect can be appreciated.

The attachment of the elastic steel wire 6 to the ringlike elastic wire rod 31 is performed simply by being passed through the filter member 3, and therefore without the need for a special structure, smooth operation can be ensured.

The second linear bodies 5 are provided, and therefore the filter member 3 can be kept in a preferable posture where the opening of the filter member 3 is orthogonal to the blood flow.

In the case where the ringlike elastic wire rod 31 is configured by winding the fine steel wire, end parts tend to be exposed in a radial direction, and may catch on the blood vessel B, tubular body 1, slide tube 21, or the like. However, in the present embodiment, as illustrated in FIG. 3, the both end excess parts 7 of the fine steel wire are extended inside the filter 32 and attached to the wire 22 so as to lie along the wire 22, so that catching and the like can be preferably prevented, and also fabrication is facilitated. In particular, in the case of using a material of which both ends are not easily welded, such as nitinol, such an effect becomes noticeable. Also, the excess parts 7 of the fine steel wire are spirally formed, so that the excess parts 7 play a role in spreading the filter 32 in the spread state, and together with the elastic steel wire 6, the filter 32 can keep a preferable configuration for capturing a thrombus or the like without being closed in the spread state. As described, in the case of, as a member, using a ring formed by multiply winding an elastic fine wire such as the fine steel wire, by extending end parts thereof to appropriately fix them to a peripheral member such as the core wire, catching and the like can be preferably prevented, and also fabrication is facilitated. At the same time, by using the elastic restoring force of the extended excess parts, a preferred action related to the spread of the filter and the like can be expected.

Variations

Figure 14:
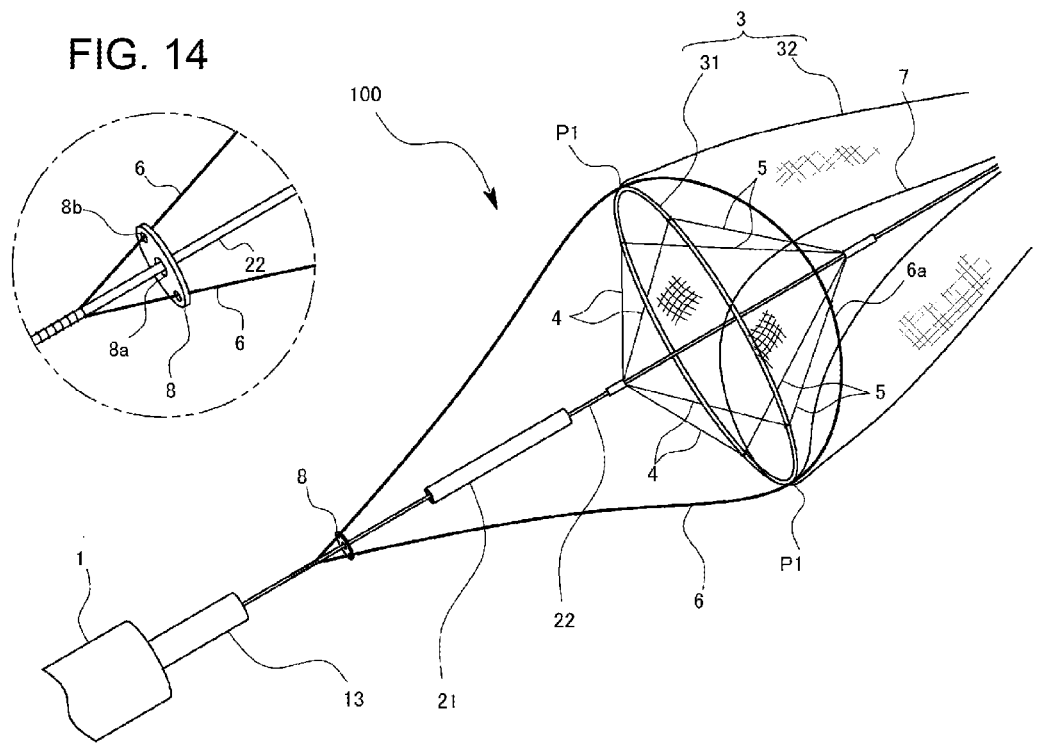
FIG. 14 is a perspective view illustrating a device for capturing debris in blood vessel in a variation of the same embodiment.
Figure 15:
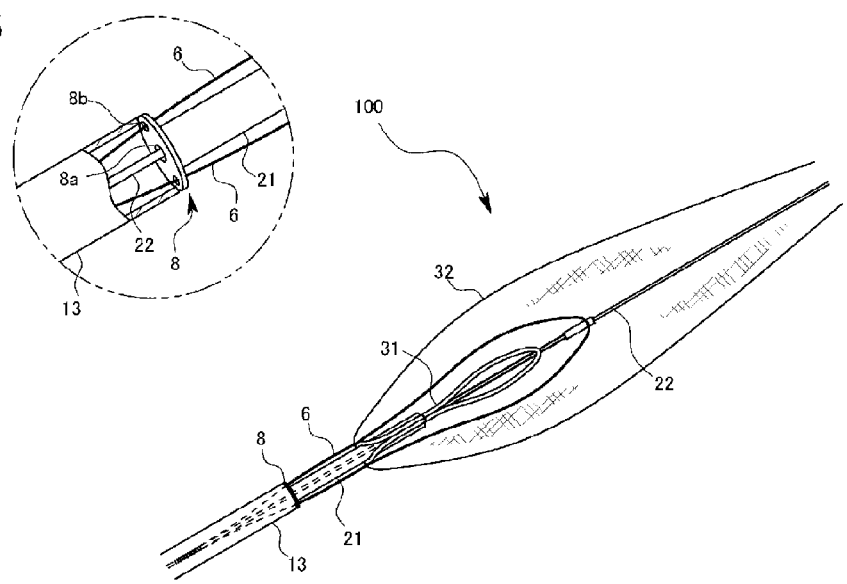
FIG. 15 is a recovery process diagram of the filter member in the same variation.

In this variation, as illustrated in FIGS. 14 and 15, a thin disk body 8 configured to, at the center thereof, open a central hole 8a through which the wire 22 passes, and around the center, open a pair of insertion holes 8b through which the elastic steel wire 6 passes is made to intervene between the slide tube 21 and the operation tube 13. Also, in the first embodiment, the diameters of the slide tube 21 and operation tube 13 are set equal to each other; however, in this variation, the diameter of the slide tube 21 is made smaller than the diameter of the operation tube 13, and the diameter of the operation tube 13 and a diameter of the disk body 8 are made almost equal to each other. The insertion holes 8b are positioned on an outer side of an outer circumference of the slide tube 21, and also positioned on an inner side of an inner circumference of the operation tube 13. This prevents the elastic steel wire 6 from being held between the operation tube 13 and the slide tube 21, and therefore a movement thereof is made smoother. Also, the diameter of the slide tube 21 can be made small, and therefore the linear bodies 4 can be brought close to more finely fold the ringlike elastic wire rod 31. Further, a problem that the slide tube 21 and the operation tube 13 come in contact with each other and cannot be separated from each other can be avoided.

Figure 16:
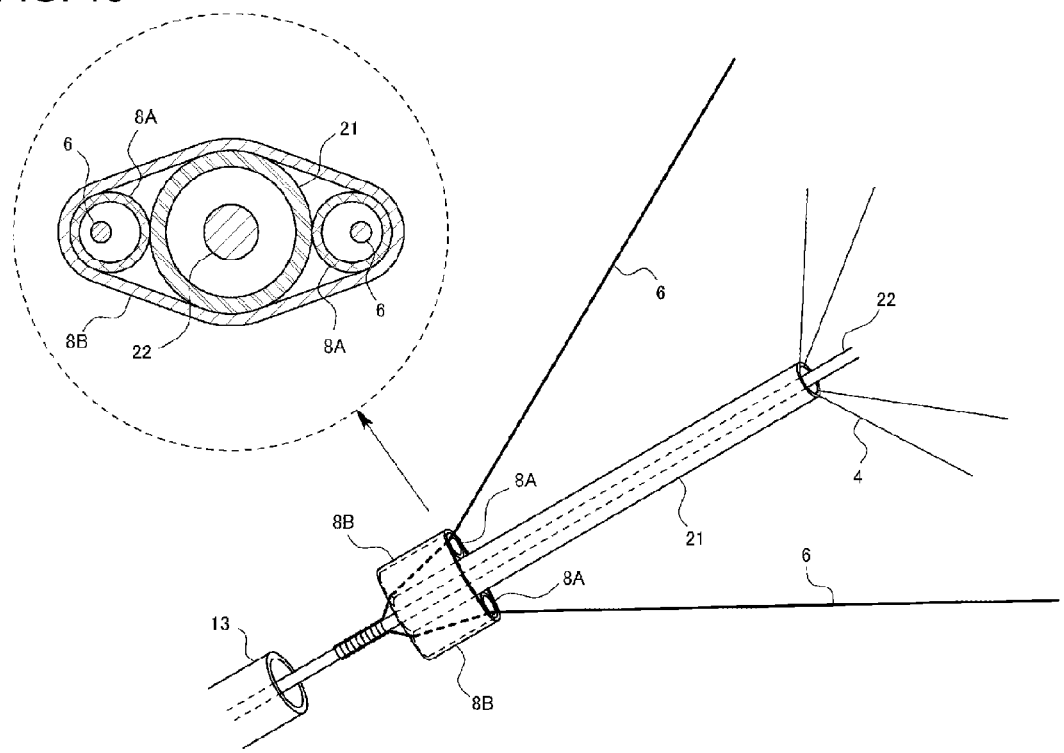
FIG. 16 is a partially enlarged perspective view illustrating a slide tube and the like in another variation of the same embodiment.

Further, for the same purpose, as illustrated in FIG. 16, a pair of short side tubes 8A may be provided on a base side of the slide tube 21. Each of the side tubes 8A is inserted with the elastic steel wire 6. This example is adapted to lay the side tubes 8A along the slide tube 21, and then fit a large diameter tube 8B at the outside of the lot of them to perform bonding fixation with a bonding adhesive. According to such a configuration, as compared with the case of opening the insertion holes in the very small and thin disk body 8, fabrication is facilitated.

Figure 17:
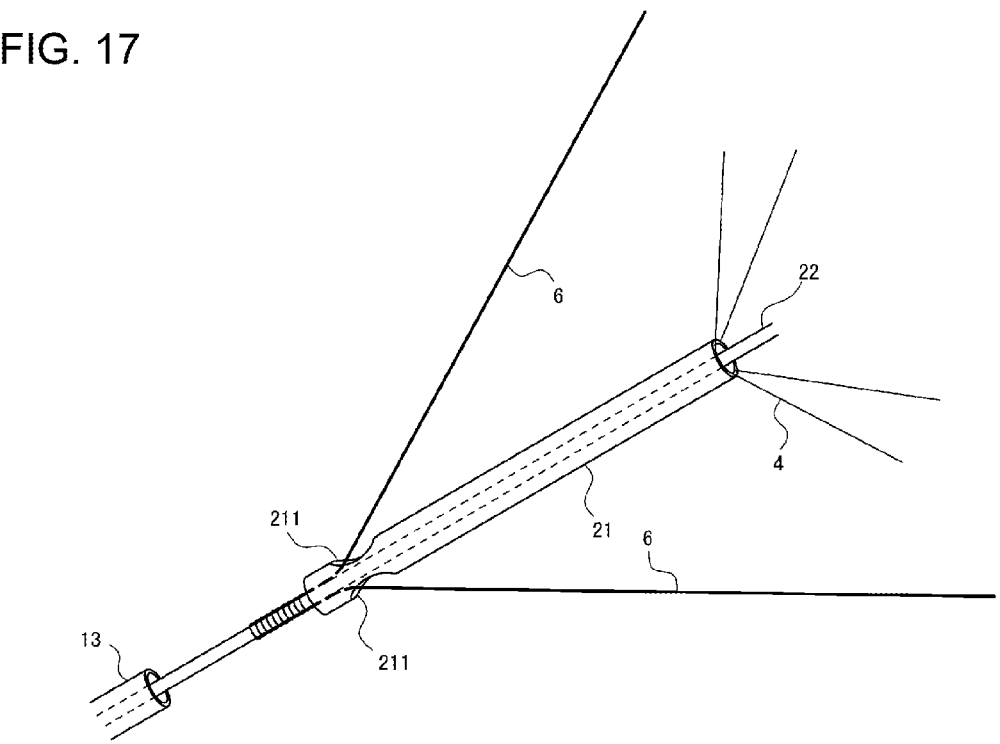
FIG. 17 is a partially enlarged perspective view illustrating a slide tube and the like in still another variation of the same embodiment.

In order to suppress the elastic steel wire 6 from being held between the operation tube 13 and the slide tube 21, and ensure smoothness of a movement, as illustrated in FIG. 17, the present invention may be adapted to, on the base side of the slide tube 21, provide a pair of opposite steel wire through-holes 211 in a lateral circumferential wall of the slide tube 21, and insert the elastic steel wire 6 into each of the steel wire through-holes 211.

Figure 18:
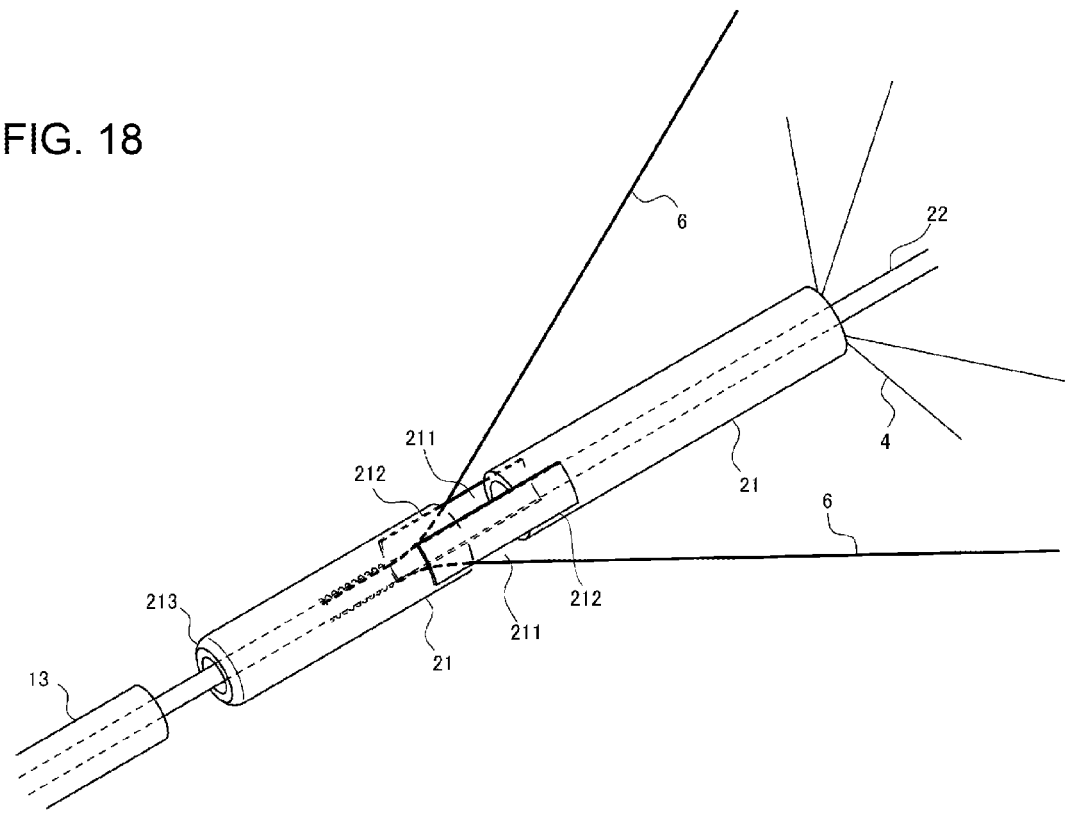
FIG. 18 is a partially enlarged perspective view illustrating a slide tube and the like in yet another variation of the same embodiment.

As illustrated in FIG. 18, the slide tube 21 may be configured to include: two tubular divided bodies; and a pair of opposite plate-like connecting members 212 that connect the divided bodies separately from each other. The elastic steel wire 6 passes through steel wire through-holes 211 formed in a gap between the connecting members 212. A basic concept is the same as a concept using the configuration in FIG. 17; however, from the viewpoint of fabrication, the configuration in FIG. 18 may be advantageous. In addition, in FIG. 18, a base end part of the slide tube 21 is contracted to provide a small diameter part 213. This results in an effect of enabling the operation tube 13 to be made thinner.

Figure 19:
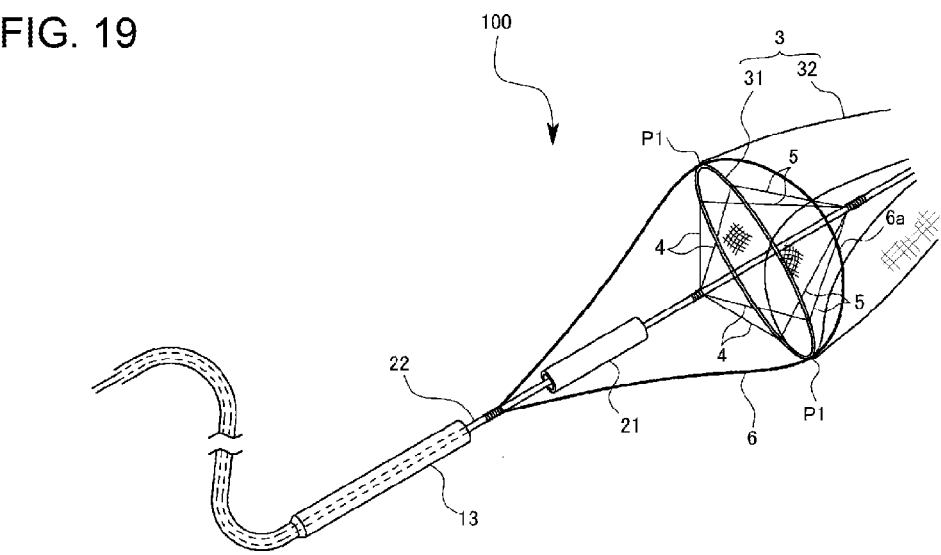
FIG. 19 is a perspective view illustrating a device for capturing debris in blood vessel in still yet another variation of the same embodiment.

As illustrated in FIG. 19, in the case of making the outside diameter of the operation tube 13 substantially equal to or less than φ0.014 inches (an outside diameter of a guide wire typically used in the case of using a balloon catheter or stent to percutaneously dilate a stenosis of a carotid artery, a coronary artery, or the like), and also inserting the wire 22 into the operation tube 13 from the beginning, the operation tube 13 can be used as a conventional guide wire for conveying a balloon catheter or a stent. In particular, in the case of making the operation tube 13 of an elastic steel tube such as a stainless steel tube or a nitinol tube, the same elasticity and rigidity as those of a typical guide wire can be obtained, which is excellent in a function of guiding (guiding function) a balloon catheter or a stent.

This concept is that a wire part (may serve as a guide wire) connecting to the filter is configured to include a tubular body (the operation tube 13 in this case), and a core wire (the wire 22 in this case) inserted into (passing through) the tubular body, based on an unprecedented new idea.

Further, such a configuration eliminates the need to insert a new operation tube for recovering the filter member 3 after the placement of the filter member 3 in a blood vessel. This is because the operation tube 13 has the function as a guide wire, and the operation tube 13 enables a blood vessel treatment tool such as a balloon catheter or a stent to be conveyed, so that the operation tube 13 can be kept in the blood vessel until the end of treatment. Even in the case of not using the operation tube 13 as a guide wire, the operation tube 13 can be kept in the blood vessel until the end of application of the filter as a protection against thrombosis. The reason for this is because the outside diameter of the operation tube 13 is extremely small, and therefore does not act as an obstacle to blood flow.

In addition, as illustrated in FIG. 19, part of the fore end part of the operation tube 13 may be slightly increased in diameter to have almost the same diameter as the diameter of the slide tube 21. This is because an outside diameter of a site where the linear bodies 4 or the like are attached to the wire 22 (core wire) may be increased, and it is necessary to pass the site.

Figure 20:
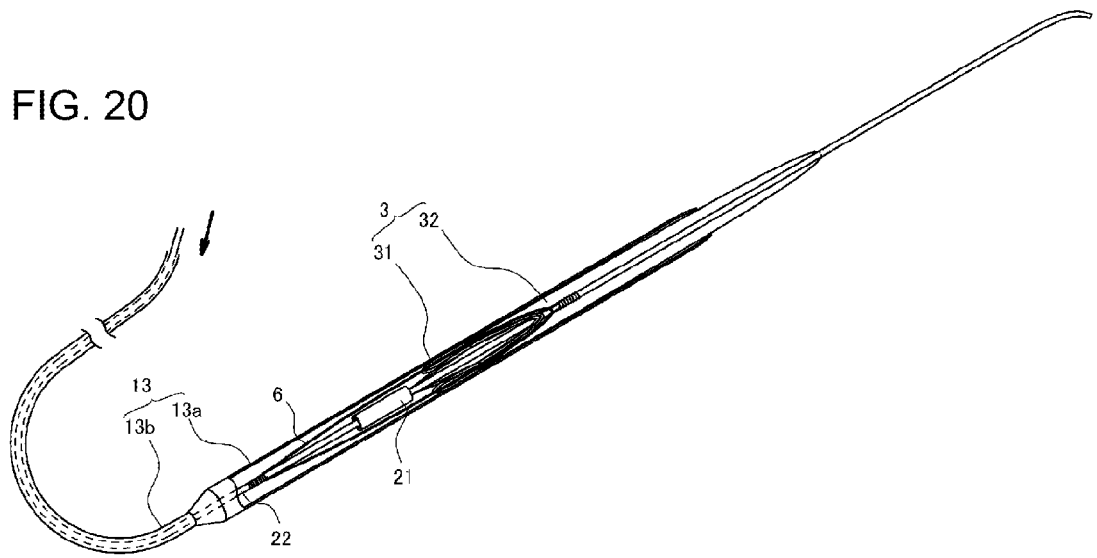
FIG. 20 is a conveyance state diagram of the filter member in a further variation of the same embodiment.
Figure 21:
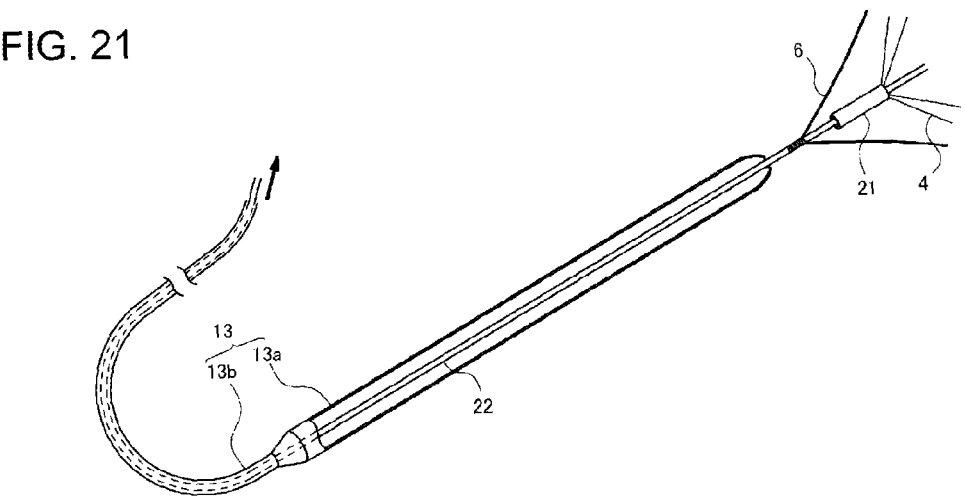
FIG. 21 is a diagram illustrating a post-conveyance state or a pre-recovery state of the filter member in the same variation.

As illustrated in FIGS. 20 and 21, the fore end part of the small diameter operation tube 13 may be configured as a storage tube 13a for storing the filter part. The storage tube 13a has a larger diameter than that of a base part 13b of the operation tube 13, and as in a storage state illustrated in FIG. 20, the storage tube 13a has the diameter that enables the filter member 3 to be stored inside. By configuring as described, the operation tube 13 also functions as a filter conveyance tube.

That is, in the case of conveying the filter member 3 with storing the filter member 3 in the operation tube 13, and after keeping the filter member 3 in a blood vessel (after releasing the filter member from the fore end of the operation tube 13), keeping the operation tube 13 on site, a balloon catheter or the like can be successively inserted for treatment of a stenosis part while being guided by the operation tube 13, and therefore it is not necessary to remove the operation tube 13.

On the other hand, after the end of a treatment operation, the fore end of the operation tube 13 is pressed against the slide tube 21, and presses the slide tube 21 forward to fold the filter member 3. The operation tube 13 is formed of a material having elastic restorability such that at this time, in this example, the fore end part of the storage tube 13a in the operation tube 13 is, as illustrated in FIG. 20, expanded in the radial direction at the time of storing the filter part, whereas as illustrated in FIG. 21, after the release, the fore end part is restored to have a diameter making it possible to press the slide tube 21, e.g., a small diameter substantially the same as that of the slide tube 21.

Figure 22:
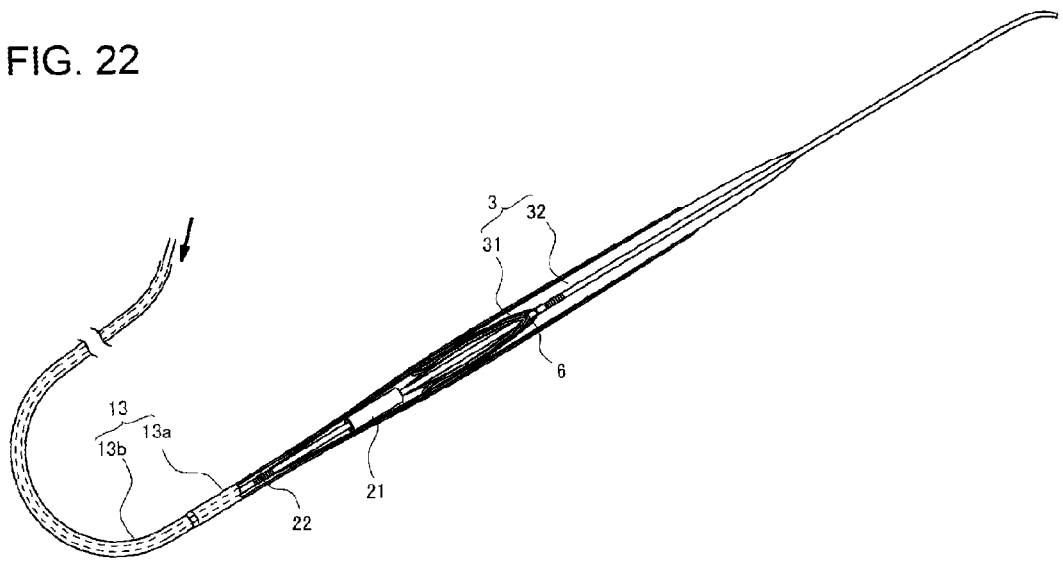
FIG. 22 is a conveyance state diagram of the filter member in a still further variation of the same embodiment.
Figure 23:
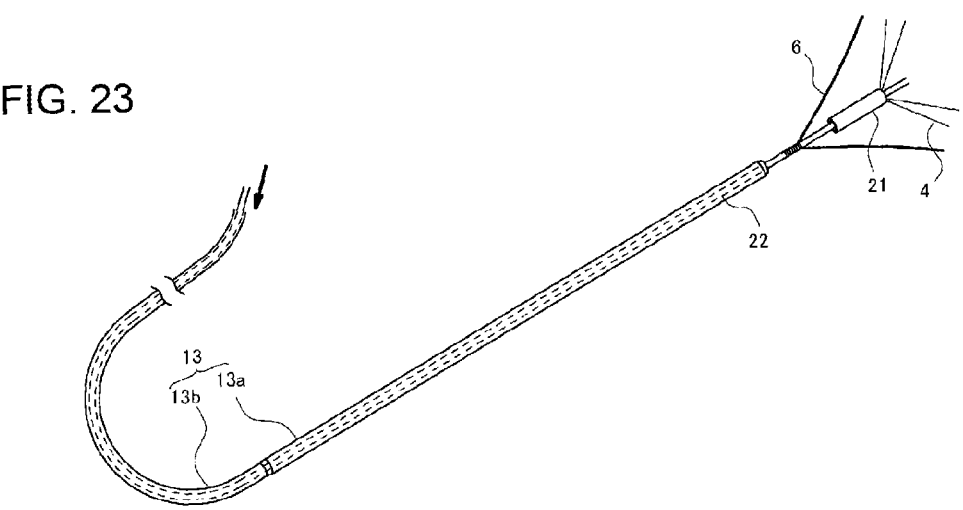
FIG. 23 is a diagram illustrating a post-conveyance state or a pre-recovery state of the filter member in the same variation.

The storage tube 13a may be one that is, as in the filter storage state illustrated in FIG. 22 and in a filter release state illustrated in FIG. 23, elastically expandable and contractable at least in the radial direction as a whole. Note that in the axial direction, rigidity for pressing the slide tube 21 is required, and therefore it is desirable to use a material having anisotropy in rigidity, such as a material having a small expansion/contraction in the axial direction and a large expansion/contraction in the radial direction.

As described above, a function of making a filter conveyance tube simultaneously fulfill a guide wire function and a function as the operation tube, i.e., a function integrating three functions, i.e., a filter conveyance function, a guide wire function, and a filter recovery function, cannot be found anywhere, and is a useful function not only for the filter but for general debris capturing filters.

In addition, in the above-described configuration using the thin tubes, the operation tube 13 is extremely thin, through which the wire 22 passes, so that in addition to a small gap between the operation tube 13 and the wire 22, the operation tube 13 and the wire 22 are kept in a blood vessel for a certain amount of time, and therefore in the case where a thrombus is formed in the gap, a mutual movement between the operation tube 13 and the wire 22 may become worse. In order to prevent this, preferably, for example, a solution sending device that forcibly and continuously sends a heparin saline solution or the like into the gap from a base is provided, and the saline solution or the like carries a function as a blood intrusion prevention solution that prevents blood from intruding into the gap.

Figure 24:
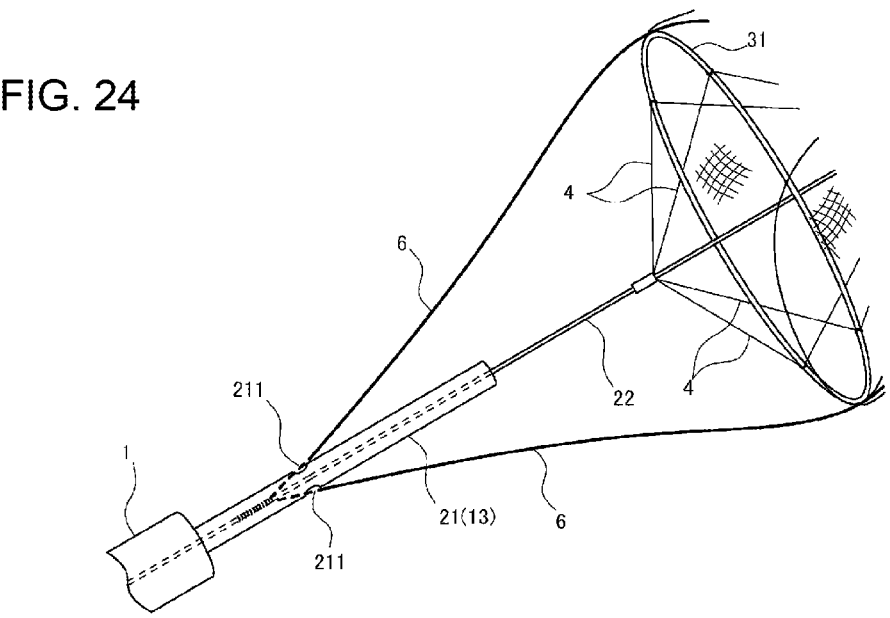
FIG. 24 is a perspective view illustrating a device for capturing debris in blood vessels in a yet further variation of the same embodiment.

Also, as illustrated in FIG. 24, the slide tube 21 and the operation tube 13 may be integrated. In FIG. 24, a pair of through-holes 211 is provided in a lateral circumferential wall of the integrated tube, and the elastic steel wire 6 attached to the wire 22 is taken outside from the through-holes 211.

Figure 25:
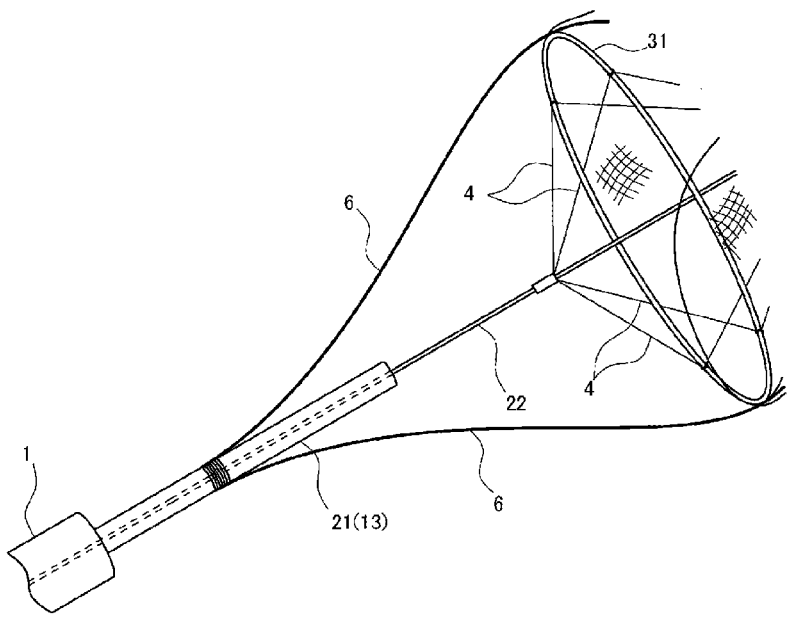
FIG. 25 is a perspective view illustrating a device for capturing debris in blood vessels in a still yet further variation of the same embodiment.

As illustrated in FIG. 25, the elastic steel wire 6 is not attached to the wire 22 but may be attached on an outer circumferential surface of the integrated slide and operation tubes 21 and 13.

Figure 27:
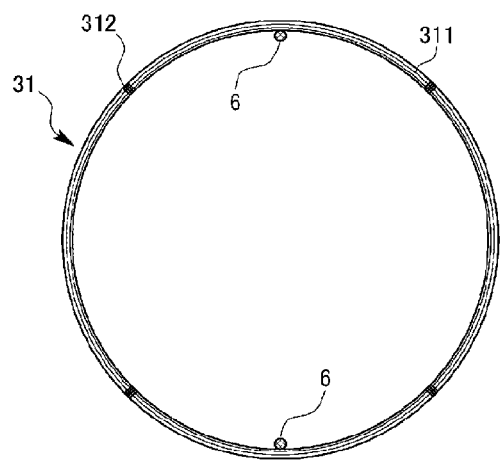
FIG. 27 is a diagram illustrating a positional relationship between the elastic steel wire and the ringlike elastic wire rod as viewed from the axial direction in still another further variation of the same embodiment.

The elastic steel wire 6 is not formed in the loop shape, but as illustrated in FIG. 26, may be formed as a pair of mutually separated wires. Also, it is only necessary that the elastic steel wire 6 is in contact with the ringlike elastic wire rod 31 at the attachment positions P1 without any gap, and for example, as illustrated in FIG. 27, the elastic steel wire 6 may pass through a radially inner side of the ringlike elastic wire rod 31.

Figure 50:
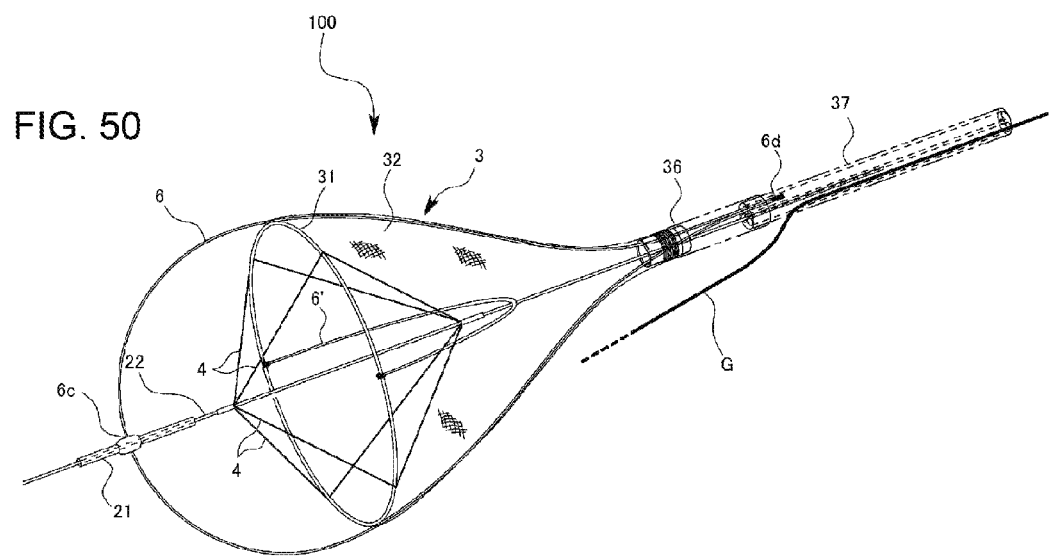
FIG. 50 is a perspective view illustrating a device for capturing debris in blood vessels in still yet another further variation of the first embodiment.

As illustrated in FIG. 50, the present invention may be adapted to fix a central part 6c of the elastic steel wire 6 to an intermediate site of the slide tube 21 with a bonding adhesive or the like, and also bring both end parts 6d together to position them on the filter 32 side. By configuring as described, force to spread the filter member 3 by the elastic steel wire 6 can be increased to surely bring the filter member 3 into the spread state.

In addition, a structure illustrated in FIG. 50 is additionally described in detail.

In FIG. 50, the present invention is configured to make the bottom part of the filter 32 together with the wire 22 slidably penetrate and protrude a fore end from the filter 32 by a predetermined length. Reference sign 36 indicates a tube member that is fixed while being penetrated through by the bottom part of the filter 32. The tube member 36 is slidably inserted with the wire 22 and both elastic steel wire end parts 6d.

A fore end part of the tube member 36 is continuously fixed with, for example, a plurality of lumen tubes 37 having a predetermined length. In FIG. 50, both elastic steel wire end parts 6d are slidably fitted into one of the lumen tubes, and also the wire 22 is fitted into another one of the lumen tubes. The present invention is adapted to be able to insert a guide wire G into still another lumen tube from a hole provided in a lateral circumferential surface. The guide wire G is used to guide the filter member 3 to a desired site in a blood vessel.

Reference sign 6' indicates a second elastic steel wire of which both end parts are attached to the ringlike elastic wire rod 31 with a phase being shifted from the elastic steel wire 6 by 90°. The second elastic steel wire 6' is adapted to be positioned inside the filter 32, and as with the elastic steel wire 6, is one that works to surely spread the filter member 3.

Figure 28:
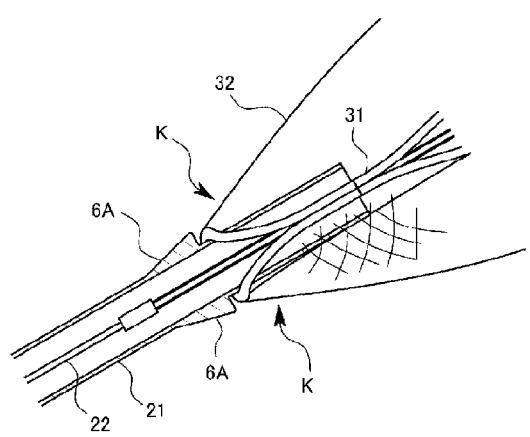
FIG. 28 is a partially enlarged view illustrating a guide member in yet another further variation of the same embodiment.

Further, it is possible to, in place of the elastic steel wire 6, use a guide member having a different shape. As a specific example, as illustrated in FIG. 28, a guide member 6A that is tapered from holding areas held by the holding parts K toward the base end side in the slide tube 21 may be integrally provided. By being guided by a tapered surface (guide surface) of the guide member 6A, the opening edge of the tubular body 1 can be suppressed from catching on any of the holding parts K. Besides, it is only necessary that the guide member is, for example, a plate-like material, and in short, only a material of which an outer surface substantially smoothly extends from fore end parts of the holding parts K toward the outer circumferential surface of the slide tube 21 is required.

Second Embodiment

Figure 29:
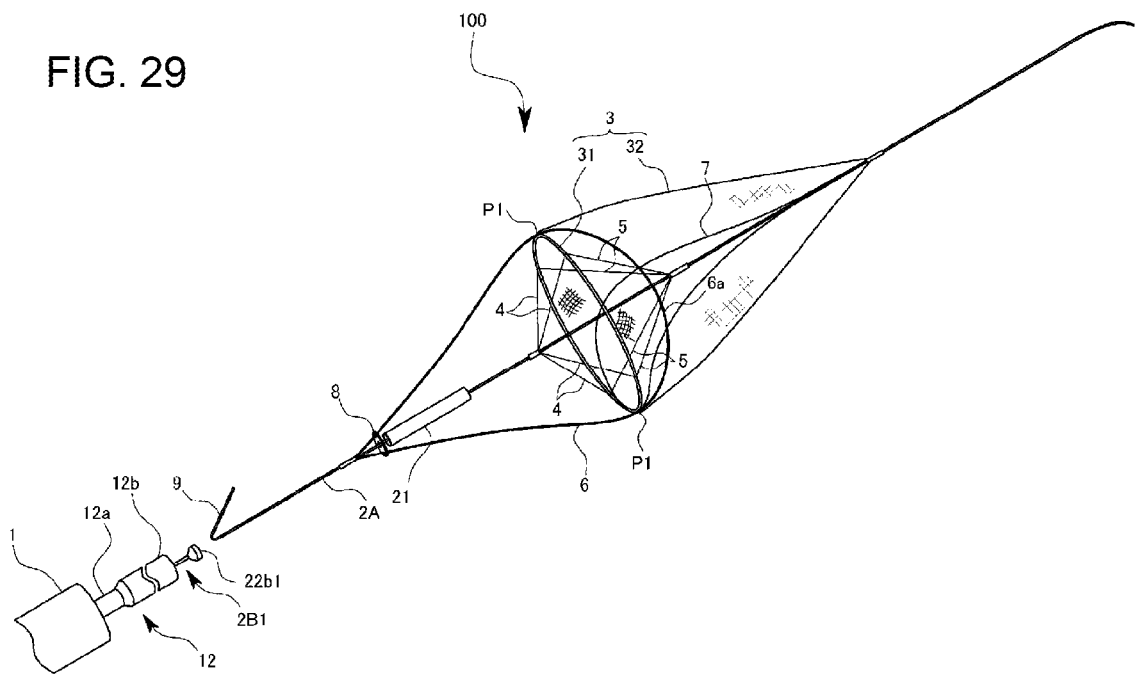
FIG. 29 is an overall perspective view illustrating a spread state of a device for capturing debris in blood vessel in a second embodiment of the present invention.

In this embodiment, as illustrated in FIG. 29, the wire in the first embodiment includes: a fore end wire 2A attached to a filter member 3; and a base wire (a conveyance base wire 2B1 or a recovery base wire 2B2) on the base side with respect to the fore end wire 2A, and the fore end wire 2A and the base wire 2B are configured to be able to be brought into contact with or separated from each other through a connecting structure.

The fore end wire 2A is, as in the first embodiment, attached to linear bodies 4, second linear bodies 5, and an elastic steel wire 6 to support the filter member 3. Also, a slide tube 21 is fitted at the outside of the fore end wire 2A. In addition, in FIG. 29, the disk body 8 cited in one of the variations of the first embodiment is provided; however, the disk body 8 is not necessarily needed.

Further, in this embodiment, a base of the fore end wire 2A is bent or curved to form a hook part 9. The fore end wire 2A is made of an elastic body, and in a natural state, configured to spread to a predetermined angle.

Next, an operating method related to placement, recovery, and the like of a device 100 for capturing debris in blood vessels having such a configuration is described.

As in the first embodiment, first, a tubular body 1 is inserted into a blood vessel B from the same direction as a flow direction of blood flow, and a fore end thereof is arranged in the upstream side vicinity of a site to place the filter member 3.

Then, a filter conveyance tube 12 of which a fore end inside stores the filter member 3 that is folded is sent from a base of the tubular body 1, and a fore end of the filter conveyance tube 12 is sent out to a placement position of the filter member 3. In addition, at this time, the hook part 9 is bent to a smaller angle than the predetermined angle and stored in the filter conveyance tube 12.

Figure 30:
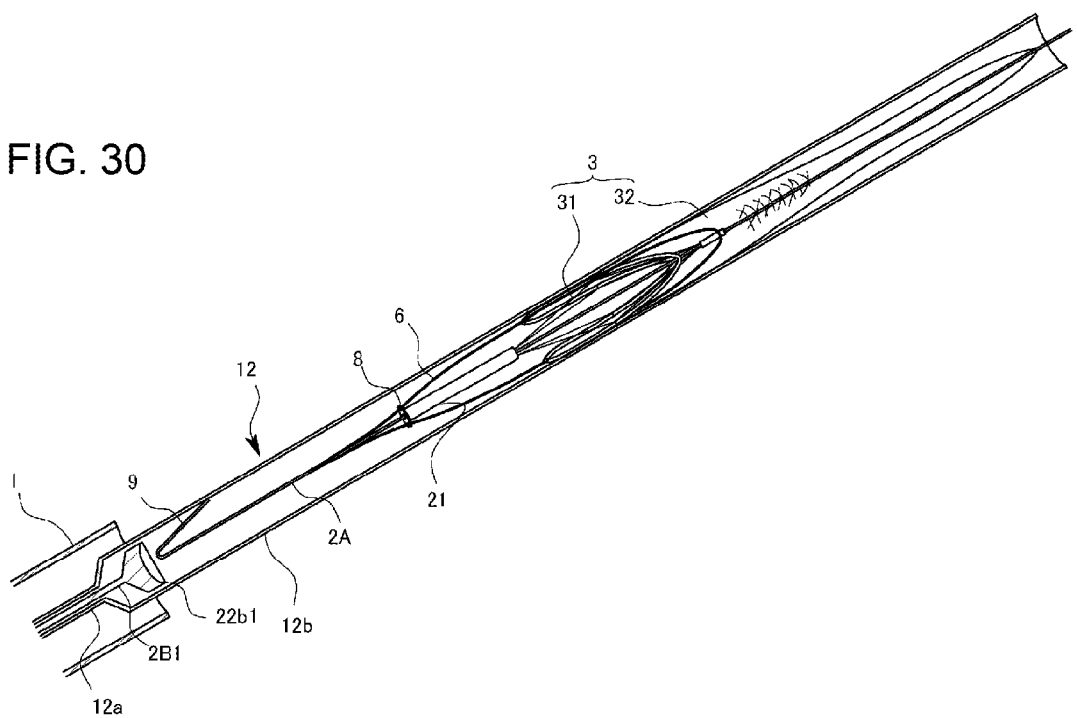
FIG. 30 is a conveyance state diagram of a filter member in the same embodiment.

At this time, the filter conveyance tube 12 is, as illustrated in FIGS. 29 and 30, adapted such that a fore end part thereof is slightly increased in diameter and is set as a storage part 12b, and in the storage part 12b, the folded filter member 3 is stored. Also, the conveyance base wire 2B1 inserted into the filter conveyance tube 12 is, at a fore end part thereof, provided with a disk-like pressing part 22b1. In addition, a fore end surface of the pressing part 22b1 is concave in this embodiment.

Subsequently, without moving the conveyance base wire 2B1, only the filter conveyance tube 12 is moved back. This causes the fore end pressing part 22b1 of the conveyance base wire 2B1 to press a base end of the fore end wire 2A, i.e., a bent part of the hook part 9, and thereby presses the filter member 3 and the fore end wire 2A attached to the filter member 3 out of the filter conveyance tube 12.

This causes an opening of the filter member 3 to be annularly spread so as to make a face direction orthogonal to the blood flow direction by the elastic restoring force of ringlike elastic wire rod 31 attached around an opening edge part of the filter member 3 and the posture binding force of the linear bodies 4 and second linear bodies 5, and thereby brought into close contact with an inner circumferential wall of the blood vessel B. Further, the hook part 9 is also spread to the predetermined angle by the elastic restoring force thereof, which is in the natural state.

After the filter member 3 has been placed as described, the filter conveyance tube 12 and the conveyance base wire 2B1 are pulled out and recovered.

Figure 31:
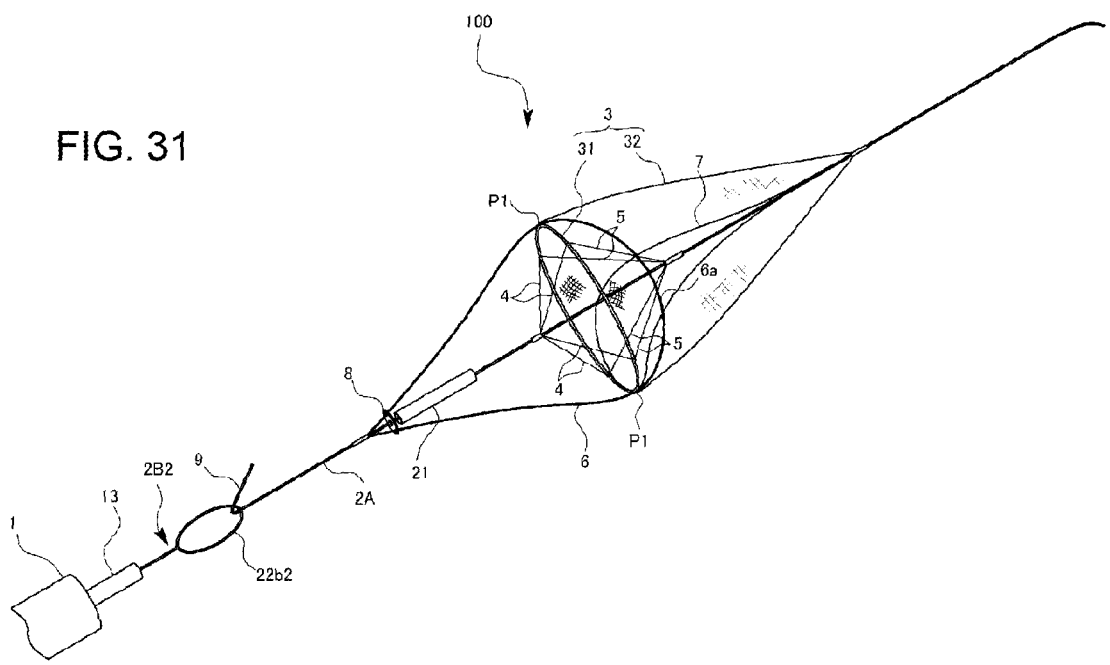
FIG. 31 is a recovery halfway state diagram of the filter member in the same embodiment.

Next, in the case of recovering the filter member 3, as illustrated in FIG. 31, an operation tube 13 is inserted into the tubular body 1 and sent out, and a fore end part thereof is protruded and positioned near the filter member 3. Further, in this state, the recovery base wire 2B2 is protruded from the operation tube 13. A fore end part of the recovery base wire 2B2 is provided with a ring part 22b2 as an engagement part.

Figure 32:
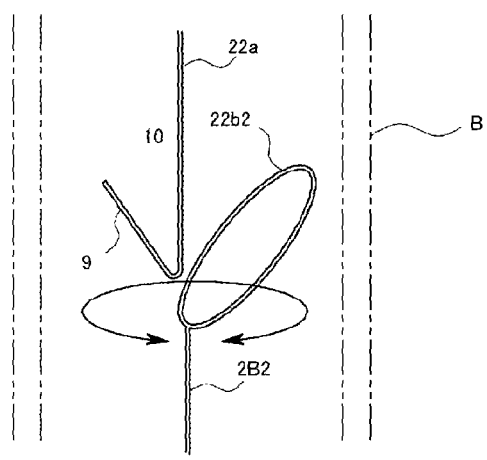
FIG. 32 is a schematic diagram illustrating a movement at the time when a ring part is made to catch a hook part in the same embodiment.

In this state, the recovery base wire 2B2 is further sent out to arrange the ring part 22b2 in almost the same position as that of the hook part 9. Then, for example, as illustrated in FIG. 32, the recovery base wire 2B2 is rotationally operated to revolve the ring part 22b2 forward and backward. This causes the ring part 22b2 to be caught by the hook part 9. Alternatively, the ring part 22b2 may be moved up and down to catch the hook part 9.

Figure 33:
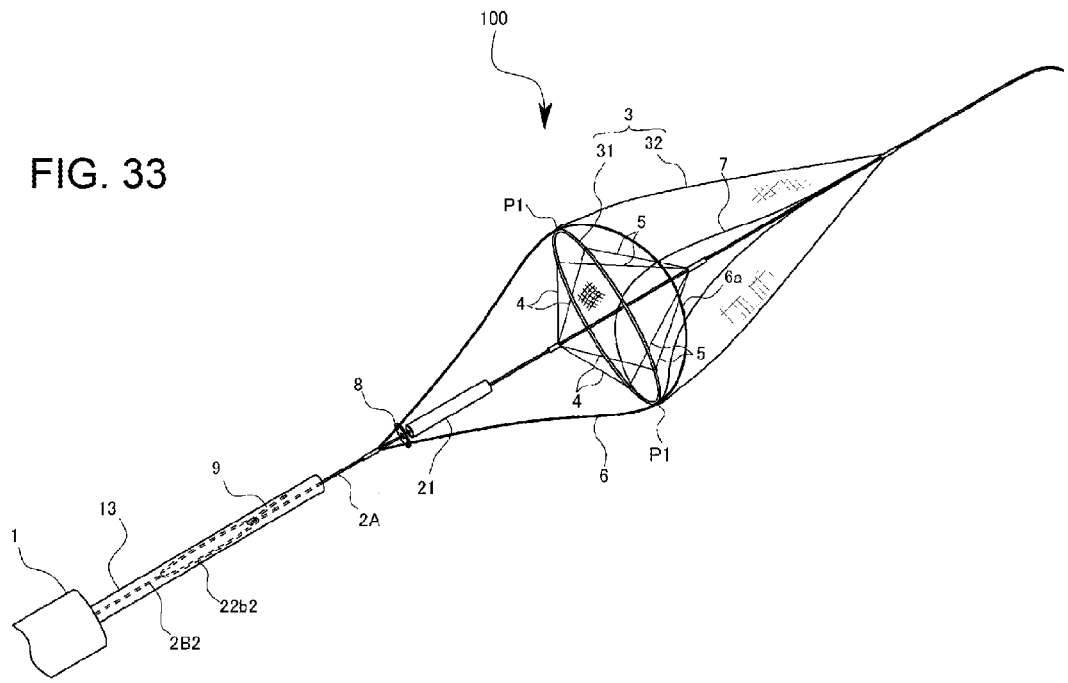
FIG. 33 is a recovery halfway state diagram of the filter member in the same embodiment.

In the case where the catch can be confirmed, the recovery base wire 2B2 is pulled in. As illustrated in FIG. 33, on the basis of this, the operation tube 13 stores inside the ring part 22b2 and hook part 9 while elastically deforming them, and further presses the slide tube 21 through the disk body 8 while being fitted at the outside of the fore end wire 2A.

Subsequent operation is the same as that in the first embodiment, and therefore description thereof is omitted.

As described, according to the present embodiment, in addition to the same effect as that of the first embodiment, the option of, during a medical operation, separating the filter member 3 from the wire to leave the filter member 3 in the blood vessel becomes possible. In practice, a wire part of a filter interferes with a maneuver, and therefore the filter cannot be sometimes used for an artificial blood vessel operation or treatment for a stent graft or the like; however, the present embodiment produces a basic effect of enabling such medical operation and treatment.

Further, the hook part 9 is one that is elastically deformed, and when released in a blood vessel, facilitates capture because a bending angle is spread, whereas at the time of conveyance, or capturing and storage, the bending angle is decreased, and therefore even in the case of thinning the operation tube 13, the hook part 9 that was spread larger than a diameter of the operation tube 13 can be reasonably stored.

Figure 34:
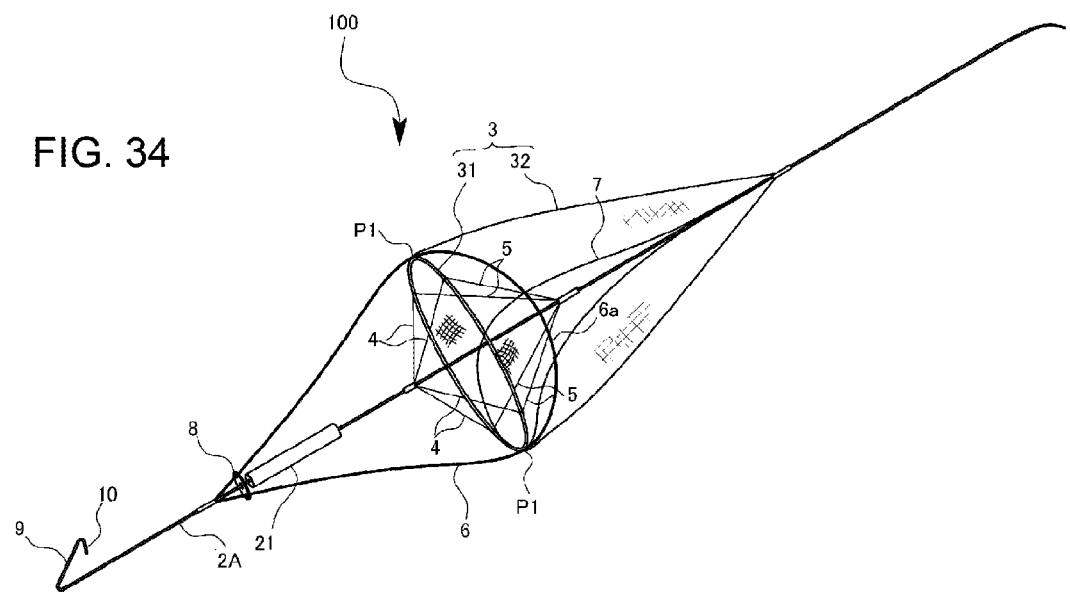
FIG. 34 is a perspective view illustrating a filter member and the like in a variation of the same embodiment.

Variations of this includes one in which, as illustrated in FIG. 34, a fore end part of the hook part 9 is further bent or curved to form a burr part 10. The burr part 10 can prevent the ring part 22b2, which has been once caught, from being removed by, for example, reverse revolution from the caught state. A reason for the forward and backward revolution is due to doing such revolving work while seeing a two-dimensional image having unclear depth such as an X-ray image.

Also, an effect of, in addition to facilitating catching, enabling an unexpected situation where during recovery, the hook part 9 and the ring part 22b2 are removed from each other in the operation tube 13 to be prevented by the burr part 10 is also obtained.

Third Embodiment

In this embodiment, a filter 32 and a ringlike elastic wire rod 31 are the same as those in the first embodiment, and therefore description thereof is omitted.

Figure 35:
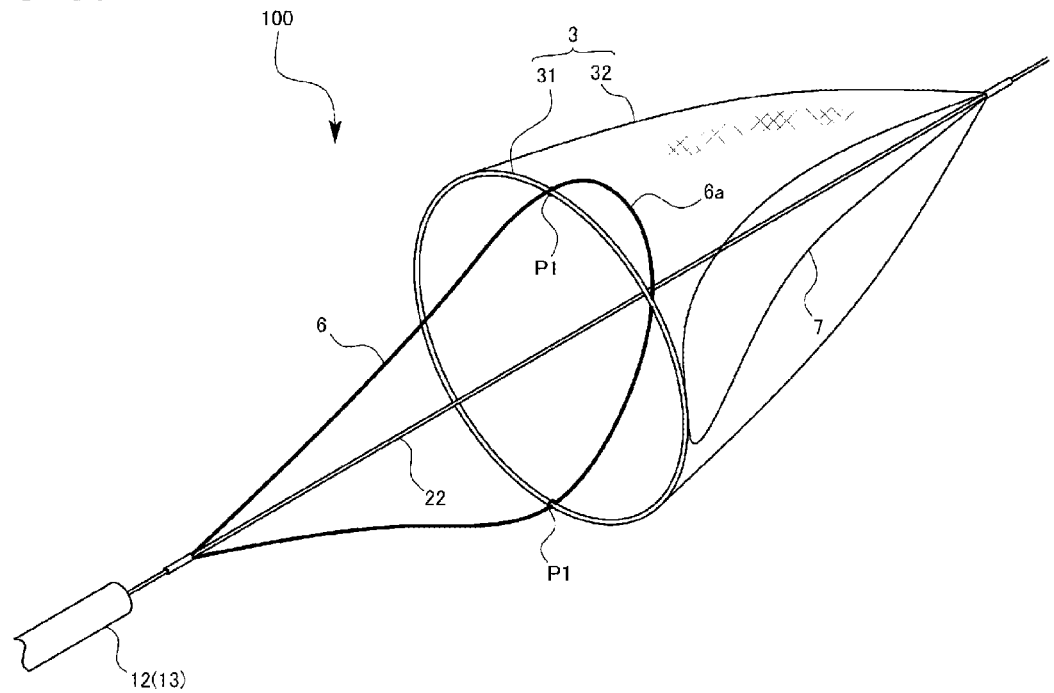
FIG. 35 is an overall perspective view illustrating a spread state of a device for capturing debris in blood vessel in a third embodiment of the present invention.

In a device 100 for capturing debris in blood vessels of this embodiment, as illustrated in FIG. 35, any linear body 4 or second linear body 5 is present, and a filter member 3 is attached to a wire 22 with an elastic steel wire 6.

The elastic steel wire 6 is, as in the first embodiment, formed in a loop shape of which both ends are attached to the wire 22 by sewing, bonding, or the like, and two opposite positions thereof are attached to two opposite positions of the ringlike elastic wire rod 31. However, differently from the first embodiment, at the attachment positions, the elastic steel wire 6 does not slide, but is fastened to the ringlike elastic wire rod 31 by winding thread or other means.

Next, an operating method related to placement, recovery, and the like of the device 100 for capturing debris in blood vessel having such a configuration is described.

First, as in the first embodiment, a tubular body (not illustrated) is inserted into a blood vessel from the same direction as a flow direction of blood flow, and a fore end thereof is arranged in the upstream side vicinity of a site to place the filter member 3.

Subsequently, a filter conveyance tube 12 is passed through the inside of the tubular body and protruded from the fore end of the tubular body, and sent out until a fore end of the filter conveyance tube 12 passes through a target stenosis part and is positioned at a periphery of the stenosis part. In a fore end part of the filter conveyance tube 12, the filter member 3 connected to the wire 22 is stored while folded.

Then, only the filter conveyance tube 12 is moved back, and thereby the wire 22 is relatively sent out of the filter conveyance tube 12 to expose the filter member 3. This causes an opening of the filter member 3 to be spread by the elastic restoring force of the ringlike elastic wire rod 31 attached around an opening edge part of the filter member 3, and upon receipt of pressure of the blood flow, as illustrated in FIG. 35, brought into close contact with an inner circumferential surface of the blood vessel in a spread state where a face direction of an opening face is orthogonal to the blood flow direction.

At this time, the elastic steel wire 6 annularly spreads so as to substantially orthogonally or obliquely intersect with the ringlike elastic wire rod 31, and a fore end side 6a with respect to the opposite positions is positioned inside the filter 32.

The filter member 3 is placed in this manner.

In the case of recovering the filter member 3, first, without moving the wire 22, an operation tube 13 as a tube member is sent out. The operation tube 13 may be the filter conveyance tube 12, or one having a different diameter from a diameter of the filter conveyance tube may be separately prepared, such as one having a smaller diameter than the diameter of the filter conveyance tube.

Figure 36:
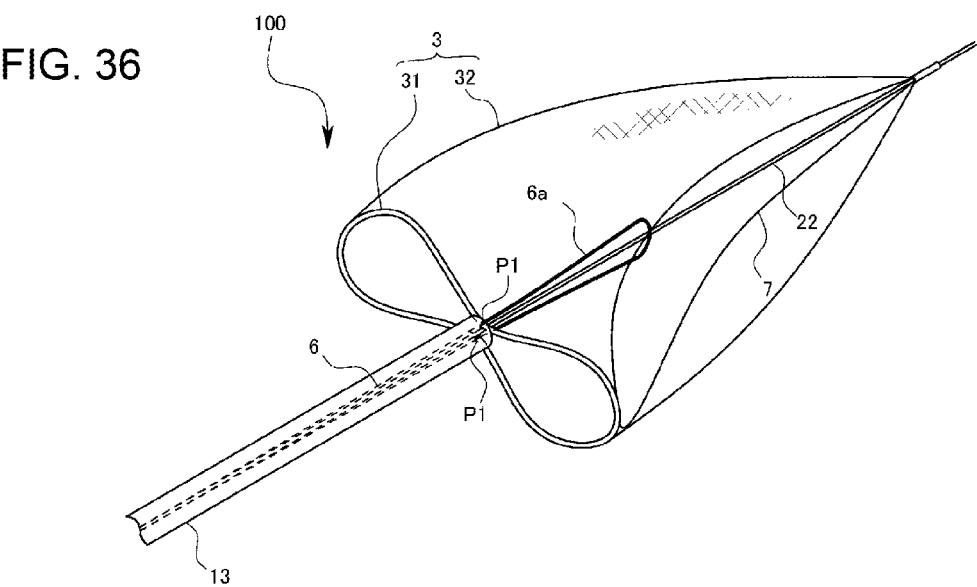
FIG. 36 is a recovery halfway state diagram of a filter member in the same embodiment.

Then, from the spread state, by relatively pulling the wire 22 into the operation tube 13 until the opposite positions of the elastic steel wire 6 are positioned at a fore end of the operation tube 13, as illustrated in FIG. 36, as the opposite positions of the elastic steel wire 6 are brought close to each other, the opposite positions P1 of the ringlike elastic wire rod 31 come close to each other, and the ringlike elastic wire rod 31 is formed in a substantially figure eight shape.

Figure 37:
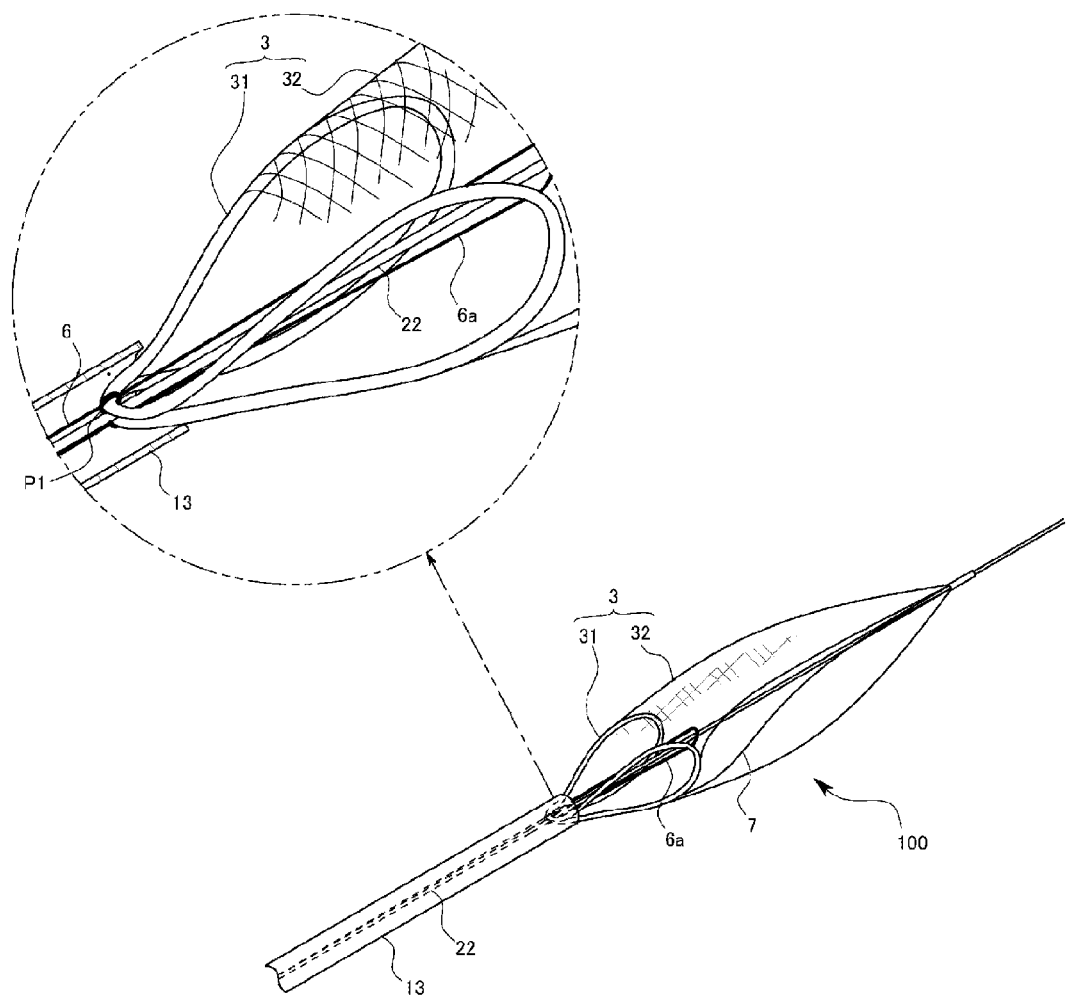
FIG. 37 is a recovery halfway state diagram of the filter member in the same embodiment.

By further relatively pulling the wire 22 into the operation tube 13 from the state of the figure eight shape, while being further bent at the respective opposite positions to reduce a width of the figure eight, the ringlike elastic wire rod 31 is, as illustrated in FIG. 37, pulled into the operation tube 13 and folded. In this state, the filter member 3 is finally stored in a tubular body 1. Note that as described in the first embodiment, a filter conveyance tube that integrates respective functions, i.e., a function as the filter conveyance tube, a guide wire function, and a function as the operation tube, can also be set.

Such a configuration is extremely simple because as opposed to the first embodiment, there are no linear bodies, and the filter member 3 is connected to the wire 22 only with the elastic steel wire. Also, the holding parts that hold the outer circumferential surface of the slide tube at the time of folding are not present, and therefore smooth recovery becomes possible without catching.

Further, the elastic steel wire 6 is formed in the loop shape, and partially fits inside the filter member 3, so that in the spread state, the elastic steel wire 6 plays a role in spreading the filter member 3, and the filter member 3 can be surely arranged in the blood vessel B in a preferable state.

In addition, the elastic steel wire 6 is formed in the loop shape, and both end parts are fastened to the wire 22 so as to lie along the wire 22, so that as described in the first embodiment, end part treatment can be made extremely easy to significantly contribute to facilitating fabrication.

Variations

Figure 38:
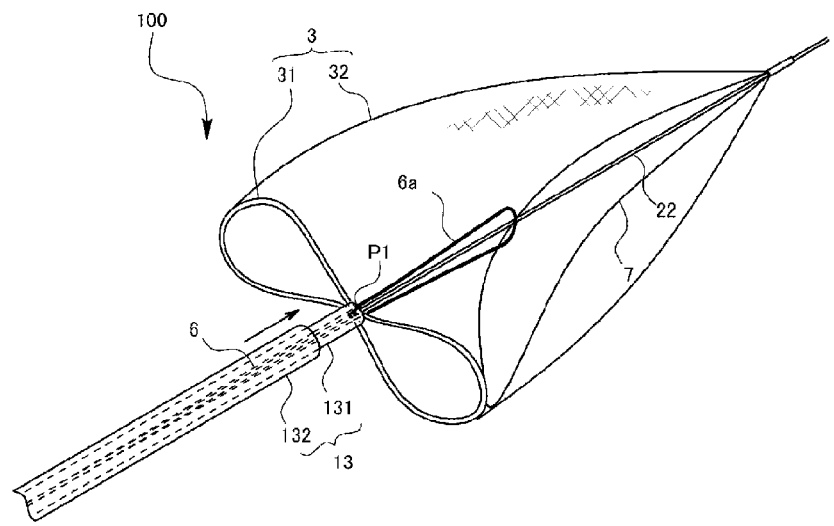
FIG. 38 is a recovery halfway state diagram of the filter member in a variation of the same embodiment.
Figure 39:
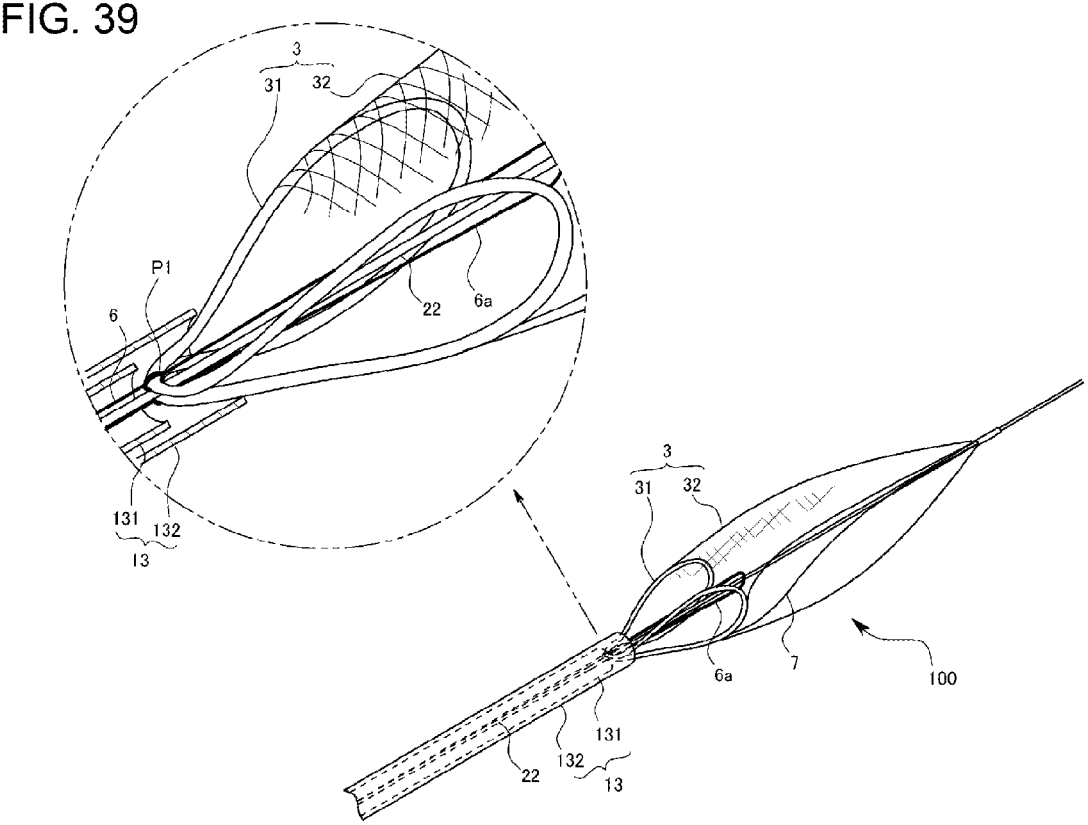
FIG. 39 is a recovery halfway state diagram of the filter member in the same variation.

The operation tube 13 may be, as illustrated in FIGS. 38 and 39, configured to include: an outer operation tube element 132; and an inner operation tube element 131 that is slidably inserted into the outer operation tube element 132, in which inside the inner operation tube element 131, the wire 22 as a core wire passes.

By configuring as described, as illustrated in FIG. 38, at least a fore end part of the inner operation tube element 131 can be made thin to form the figure eight shape in which the opposite positions of the ringlike elastic wire rod 31 are in closer contact with each other, and therefore it can be expected to form a smaller folded shape.

However, the inner operation tube element 131 is thin, and in such a state, it is impossible to pull the ringlike elastic wire rod 31 into the inner operation tube element 131 to bend the ringlike elastic wire rod 31. Accordingly, in the state illustrated in FIG. 38 where the ringlike elastic wire rod 31 is formed in the figure eight shape, the outer operation tube element 132 preliminarily inserted with the inner operation tube element 131 is sent out, and as illustrated in FIG. 39, the ringlike elastic wire rod 31 is bent by the outer operation tube element 132, and then recovered inside the outer operation tube element 132 while folded.

Note that the tubular body 1 described in the above embodiment and the operation tube may be respectively regarded as the outer operation tube element and the inner operation tube element, and made to perform the same operations.

Fourth Embodiment

This embodiment is one adapted to incorporate an idea of separating a filter member 3, which is an idea as in the second embodiment, in the third embodiment.

That is, a wire in this embodiment includes: a fore end wire 2A attached to the filter member 3; and a base wire (a conveyance base wire 2B1 or a recovery case wire 2B2) on a base side with respect to the fore end wire 2A. Also, the fore end wire 2A and the base wire 2B are configured to be able to be brought into contact with or separated from each other through a connecting structure.

Figure 40:
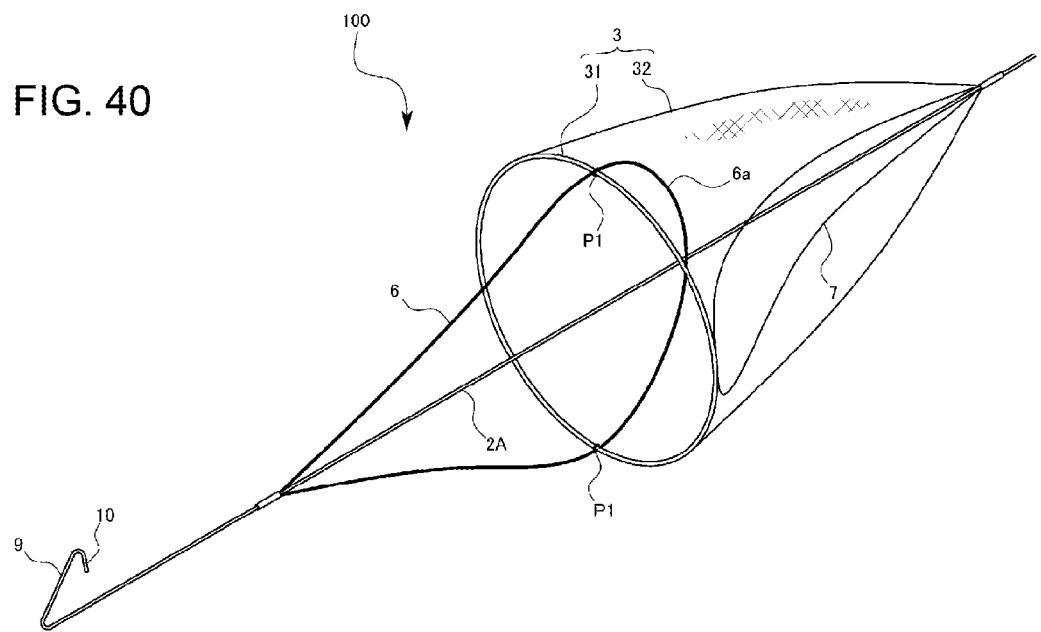
FIG. 40 is a perspective view illustrating a spread state of a filter member in a fourth embodiment of the present invention.

The fore end wire 2A is, as illustrated in FIG. 40, attached to the filter member 3 through an elastic steel wire 6 as in the third embodiment. Also, as in the second embodiment, a base of the fore end wire 2A is bent or curved to form a hook part 9.

Next, an operating method related to placement, recovery, and the like of a device 100 for capturing debris in blood vessels having such a configuration is described.

As in the first embodiment, first, a tubular body (not illustrated) is inserted into a blood vessel from the same direction as a flow direction of blood flow, and a fore end thereof is arranged in the upstream side vicinity of a site to place the filter member 3.

Figure 41:
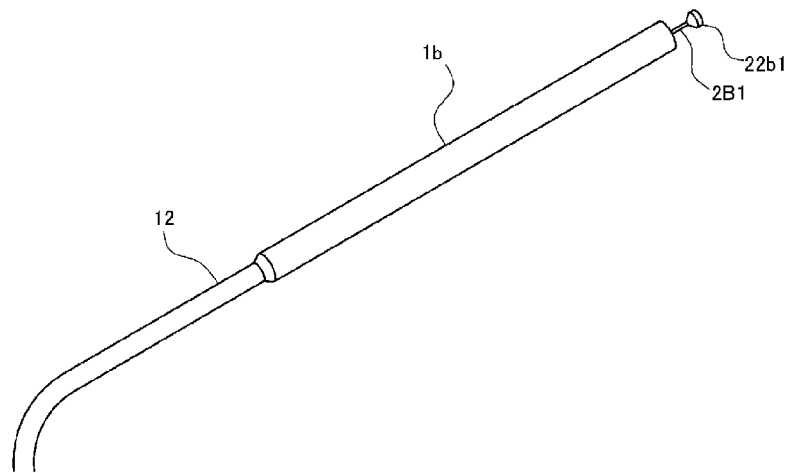
FIG. 41 is a perspective view illustrating a filter conveyance tube and a conveyance base wire in the same embodiment.

Subsequently, a filter conveyance tube 12 is passed through the inside of the tubular body and protruded from a fore end of the tubular body, and sent out until a fore end of the filter conveyance tube 12 passes through a target stenosis part and is positioned at a periphery of the stenosis part. A fore end part of the filter conveyance tube 12 is, as illustrated in FIG. 41, formed with a storage part 1b that is formed to have a slightly large diameter, and inside the storage part 1b, the folded filter member 3 and the fore end wire 2A are stored. Also, the conveyance base wire 2B1 is, at a fore end part thereof, provided with a disk-like pressing part 22b1.

Then, without moving the conveyance base wire 2B1, only the filter conveyance tube 12 is moved back. This causes the fore end pressing part 22b1 of the conveyance base wire 2B1 to press a base end of the fore end wire 2A, i.e., a bending part of the hook part 9 to press the filter member 3 and the fore end wire 2A attached to the filter member 3 out of the filter conveyance tube 12.

As a result, an opening of the filter member 3 is spread by the elastic restoring force of a ringlike elastic wire rod 31 attached around an opening edge part of the filter member 3, and upon receipt of pressure of the blood flow, an opening face is brought into close contact with an inner circumferential wall of the blood vessel B in a posture where a face direction is orthogonal to the blood flow direction. The filter member 3 is placed in this manner. Also, the conveyance base wire 2B1 is pulled out and recovered.

Figure 42:
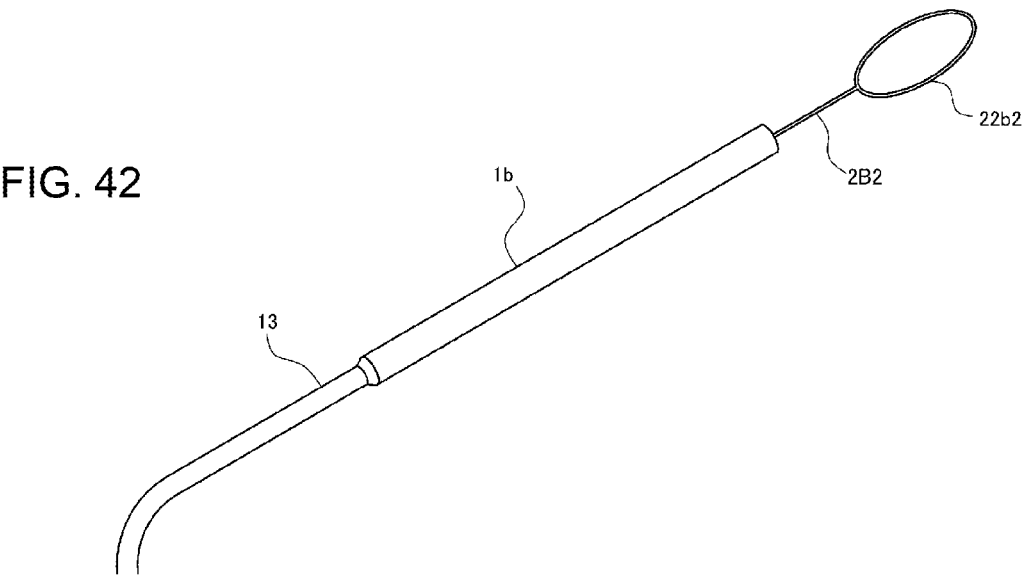
FIG. 42 is a perspective view illustrating an operation tube and a recovery base wire in the same embodiment.
Figure 43:
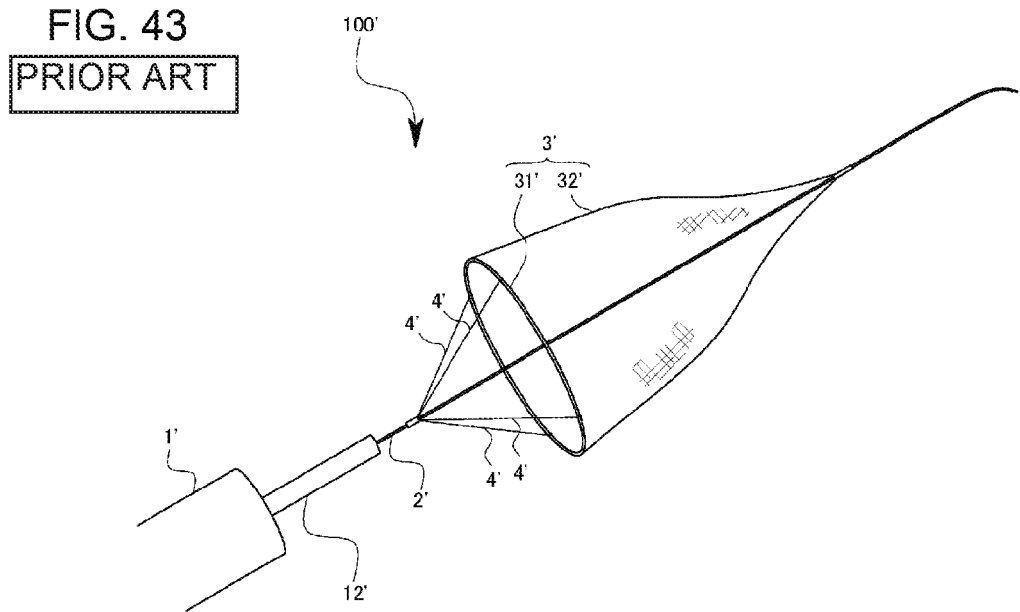
FIG. 43 is an overall perspective view illustrating a spread state at the time of placing a debris capturing device in a conventional example.
Figure 44:
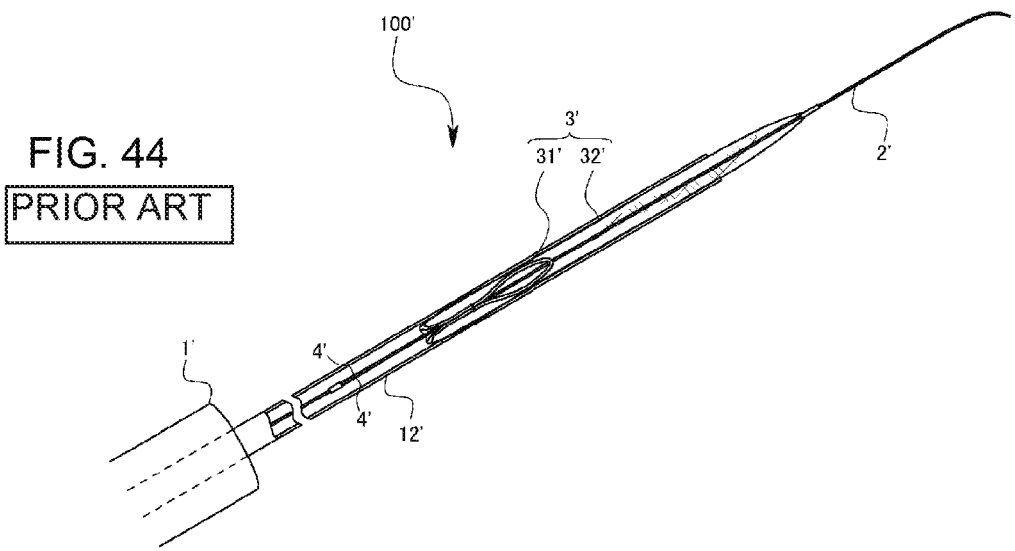
FIG. 44 is a conveyance estate diagram of a filter member in the conventional example.
Figure 45:
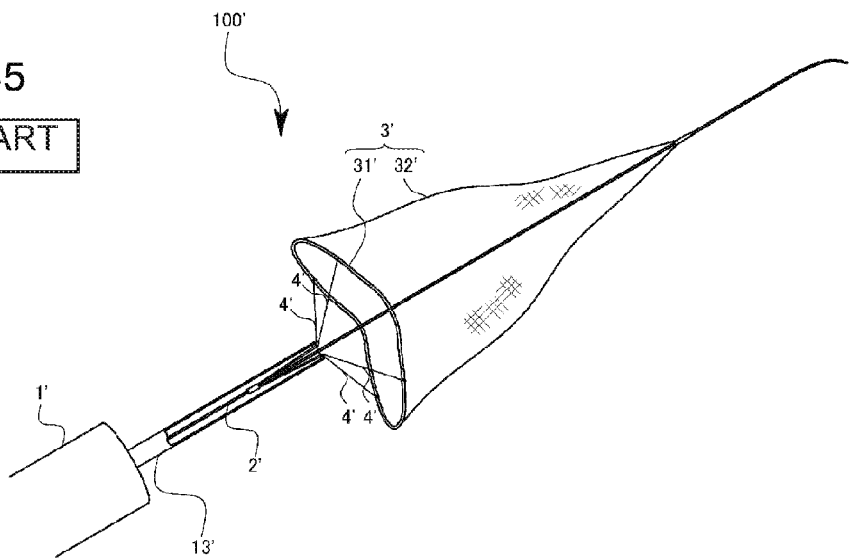
FIG. 45 is a recovery start state diagram of the filter member in the conventional example.
Figure 46:
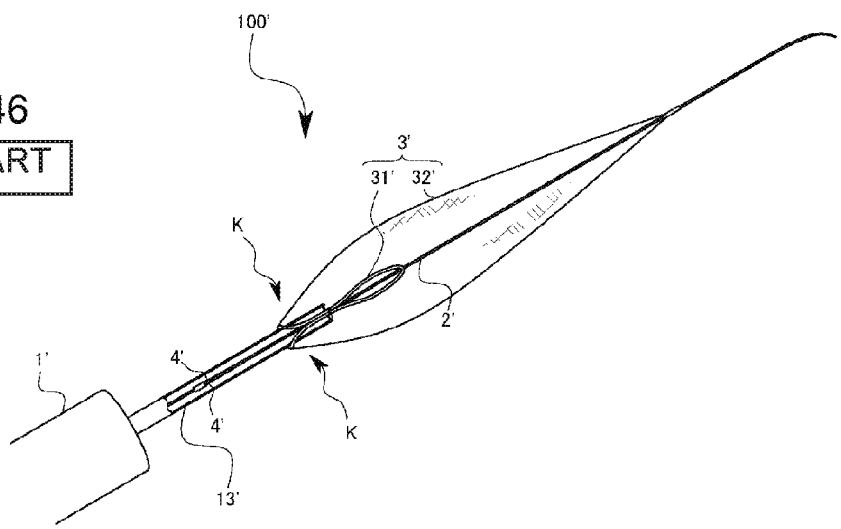
FIG. 46 is a recovery halfway state diagram of the filter member in the conventional example.
Figure 47:
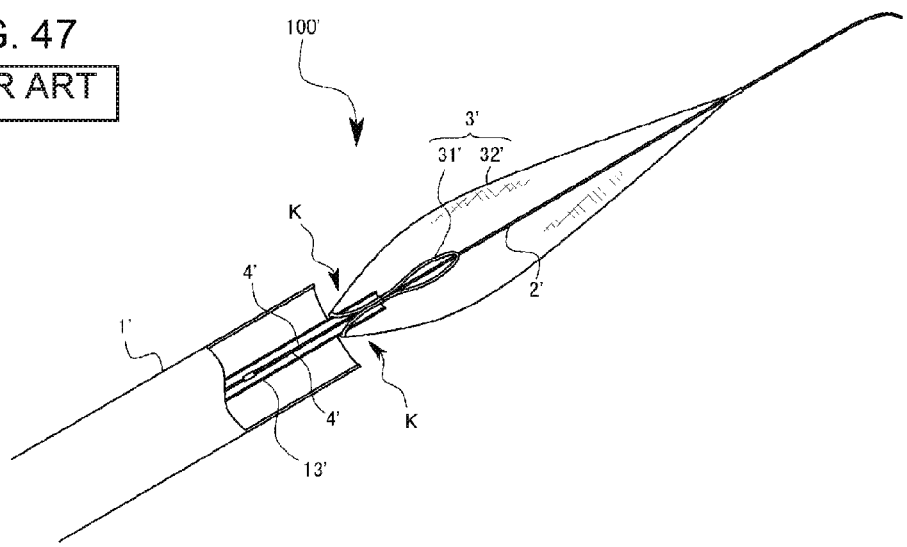
FIG. 47 is a recovery halfway state diagram of the filter member in the conventional example.
Figure 48:
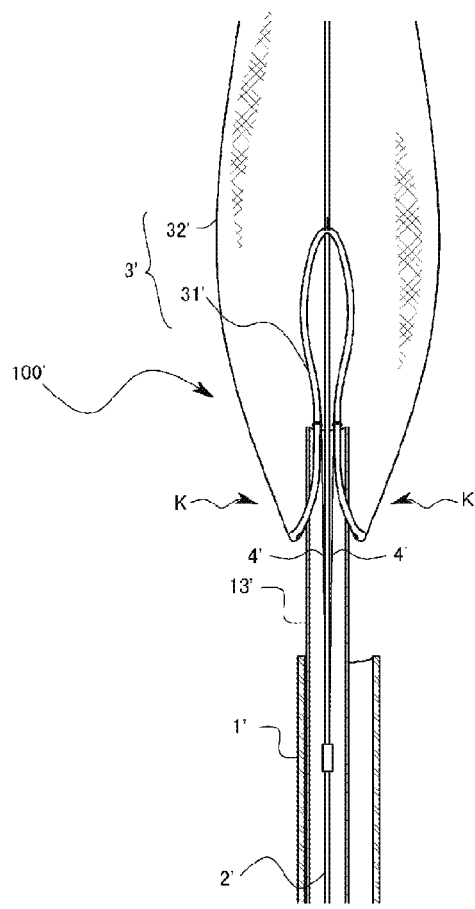
FIG. 48 is a diagram illustrating a catch in the process of recovering the filter member in the conventional example.
Figure 49:
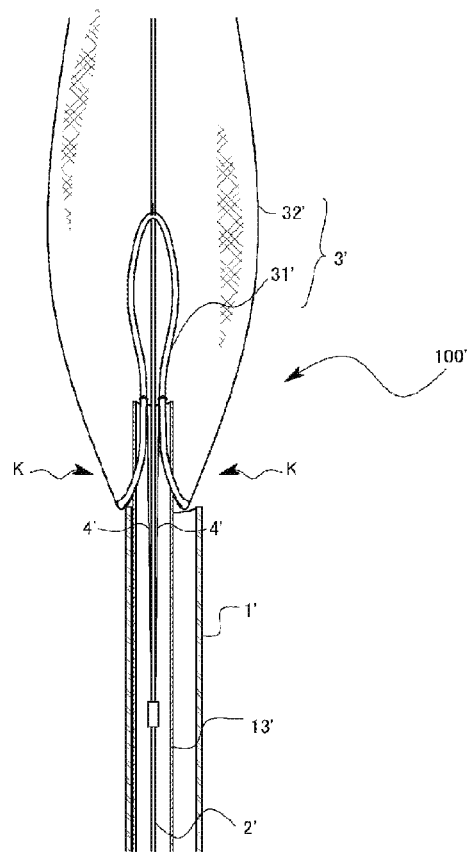
FIG. 49 is a diagram illustrating the catch in the process of recovering the filter member in the conventional example.

Next, in the case of recovering the filter member 3, the conveyance base wire 2B2 is inserted into an operation tube 13 and sent out, and a fore end thereof is protruded and positioned at almost the same position as that of the hook part 9 of the fore end wire 2A. The recovery base wire 2B2 is formed of a steel wire, and as illustrated in FIG. 42, the fore end part thereof is provided with a ring part 22b2 as an engagement part. Note that the operation tube 13 may be the filter conveyance tube 12, or one having a different diameter from a diameter of the filter conveyance tube may be separately prepared.

Then, as in the second embodiment, the recovery base wire 2B2 is operated rotationally or up and down to make the ring part 22b2 catch the hook part 9. Subsequently, the operation tube 13 is sent out to store the ring part 22b2 and hook part 9 inside thereof with deforming the ring part 22b2 and hook part 9, and then fitted at the outside of the fore end wire 2A.

Subsequent steps are the same as those in the third embodiment, and therefore description thereof is omitted.

In addition, it should be appreciated that the present invention is not limited to any of the above-described embodiments, but can be variously modified unless contrary to the scope thereof, such as appropriate combinations of partial elements of the respective embodiment.

INDUSTRIAL APPLICABILITY

According to the present invention, even in the case where when at the time of recovering the filter member, the filter member is fitted into the tubular body from the fore end opening of the tubular body, the fore ends of the holding parts are slightly displaced from the outer circumferential surface of the slide tube, the guide member is present between the fore ends and the outer circumferential surface to play a role in sliding at the opening edge of the tubular body, and therefore the fore end opening edge of the tubular body does not fits into any of the gaps between the outer circumferential surface of the slide tube and the holding parts. Accordingly, without any of the holding parts being caught by the opening edge of the tubular body, the filter member can be smoothly pulled into the tubular body.

The invention claimed is:

1. A device for capturing debris in blood vessels, the device comprising:
    a core wire configured to be arranged in a blood vessel;
    a filter member that includes a baglike filter configured to be arranged in the blood vessel such that an opening faces an upstream side of blood flow, and a ringlike elastic wire rod that is attached around an opening edge part of the filter to be, in a spread state, formed in an annular shape spread by an elastic restoring force thereof, can be brought into two states, the two states comprising a folded state and the spread state of being spread in the blood vessel, and is attached to the core wire;
    a plurality of linear bodies of which one end parts are respectively attached to a plurality of positions of the ringlike elastic wire rod and the other end parts are attached on a base side of the core wire with respect to the one end parts, the plurality of linear bodies connecting the filter member to the core wire; and
    a slide tube inside which the core wire passes,
    the device configured such that, in a case of moving the slide tube toward a fore end side of the core wire from the spread state to thereby pull the linear bodies into the slide tube from the other end parts, the one end parts of the respective linear bodies and the plurality of positions of the ringlike elastic wire rod come close to each other, the plurality of positions being respectively attached to the one end parts, and the ringlike elastic wire rod is bent so as to hold a fore end part outer circumferential surface of the slide tube from radially outside, and brought into the folded state,
    further comprising a guide member having a guide surface that is, in the folded state, substantially formed between an outer side of a fore end part of a holding part in the ringlike elastic wire rod and an outer circumferential surface of the slide tube on a base side with respect to the fore end part.

2. The device for capturing debris in blood vessels according to claim 1, configured to move an operation tube toward the fore end side of the core wire and thereby make a fore end of the operation tube press the slide tube to move the slide tube toward the fore end side of the core wire, the operation tube being arranged on a base side of the slide tube and guided by the core wire to move forward and backward.

3. The device for capturing debris in blood vessels according to claim 1, wherein
    the guide member is an elastic wire having a predetermined flexural rigidity.

4. The device for capturing debris in blood vessels according to claim 3, wherein
    the elastic wire is, at a base end part thereof, attached to the core wire, extends in a direction toward a fore end of the core wire while passing through an outer side of the slide tube from a base end attachment site thereof, or extends in the direction toward the fore end of the core wire while passing through an inner side of the slide tube from the base end attachment site and extending toward the outer side of the slide tube from a wire through-hole provided in a lateral circumferential wall of the slide tube, and is slidably attached to the fore end part of the holding part along an extending direction of the core wire.

5. The device for capturing debris in blood vessels according to claim 4, wherein
the elastic wire is attached to a radially outer side of the fore end part of the holding part.

6. The device for capturing debris in blood vessels according to claim 3, wherein
the ringlike elastic wire rod forms a pair of opposite holding parts in the folded state, wherein
a pair of elastic wires provided correspondingly to the respective holding parts is configured to extend inside the filter from fore end parts of the respective holding parts, and integrally connect to each other to form a loop shape.

7. The device for capturing debris in blood vessels according to claim 1, further comprising
a plurality of second linear bodies of which one end parts are respectively attached to a plurality of positions of the ringlike elastic wire rod and the other end parts are attached on the fore end side of the core wire with respect to the one end parts, the plurality of second linear bodies connecting the ringlike elastic wire rod to the core wire.

8. The device for capturing debris in blood vessels according to claim 1, wherein
the ringlike elastic wire rod is configured by winding a thin wire, and both end excess parts of the thin wire extend inside the filter and are attached to the core wire.

9. The device for capturing debris in blood vessels according to claim 1, wherein
the core wire is configured to be able to bring or separate a fore end core wire that is attached to the filter member and passes through the slide tube into contact with or from a base core wire on a base side with respect to the fore end core wire, wherein
as the base core wire, two types are provided, the two types comprising a conveyance core wire used at a time of placing the filter member in the blood vessel and a recovery core wire used at a time of recovering the filter member from the blood vessel,
a fore end part of the conveyance core wire is provided with a pressing surface that presses an engaged part provided in a base end part of the fore end core wire without engaging with the engaged part, and
a fore end part of the recovery core wire is provided with an engaging part that engages with the engaged part.

10. The device for capturing debris in blood vessels according to claim 9, wherein
the engaged part is a hook part that is formed by bending the base end part of the fore end core wire toward the fore end side, and the hook part is configured to, at a time of placing the filter member in the blood vessel, spread an angle formed with the fore end core wire by an elastic restoring force thereof.

11. A device for capturing debris in blood vessels comprising:
a core wire configured to be arranged in a blood vessel;
a filter member that includes a baglike filter configured to be arranged in the blood vessel such that an opening faces an upstream side of blood flow, and a ringlike elastic wire rod attached around an opening edge part of the filter to be, in a spread state, formed in an annular shape spread by an elastic restoring force thereof, can be brought into two states, the two states comprising a folded state and the spread state of being spread in the blood vessel, and is attached to the core wire; and
an elastic wire that is, in a natural state, formed in an annular shape spread by an elastic restoring force thereof, wherein one position thereof is attached to the core wire and arranged on a base end side, and opposite positions on a fore end side with respect to the position of the attachment to the core wire are respectively attached to opposite positions of the ringlike elastic wire rod, wherein
the elastic wire is configured to be able to converge along the core wire to thereby deform the filter member from the spread state to the folded state; in the spread state, annularly spread so as to intersect with the ringlike elastic wire rod; and position a fore end side with respect to the opposite positions inside the filter; and wherein
the ringlike elastic wire rod is configured by winding a thin wire, and both end excess parts of the thin wire are extended inside the filter and attached to the core wire.

12. A device for capturing debris in blood vessels comprising:
a core wire configured to be arranged in a blood vessel;
a filter member that includes a baglike filter configured to be arranged in the blood vessel such that an opening faces an upstream side of blood flow, and a ringlike elastic wire rod attached around an opening edge part of the filter to be, in a spread state, formed in an annular shape spread by an elastic restoring force thereof, can be brought into two states, the two states comprising a folded state and the spread state of being spread in the blood vessel, and is attached to the core wire; and
an elastic wire that is, in a natural state, formed in an annular shape spread by an elastic restoring force thereof, wherein one position thereof is attached to the core wire and arranged on a base end side, and opposite positions on a fore end side with respect to the position of the attachment to the core wire are respectively attached to opposite positions of the ringlike elastic wire rod, wherein
the elastic wire is configured to: be able to converge along the core wire to thereby deform the filter member from the spread state to the folded state; in the spread state, annularly spread so as to intersect with the ringlike elastic wire rod; and position a fore end side with respect to the opposite positions inside the filter, and wherein
the core wire is configured to be able to bring or separate a fore end core wire attached to the filter member and the elastic wire and a base core wire on a base side with respect to the fore end core wire into contact with or from each other, wherein
as the base core wire, two types are provided, the two types comprising a conveyance core wire used at a time of placing the filter member in the blood vessel and a recovery core wire used at a time of recovering the filter member from the blood vessel,
a fore end part of the conveyance core wire is provided with a pressing surface that presses an engaged part provided in a base end part of the fore end core wire without engaging the engaged part; and
a fore end part of the recovery core wire is provided with an engaging part that engages with the engaged part.

13. The device for capturing debris in blood vessels according to claim 12, wherein
the engaged part is a hook part that is formed by bending the base end part of the fore end core wire toward the fore end side, and the hook part is configured to, at a time of placing the filter member in the blood vessel, spread an angle formed with the fore end core wire by an elastic restoring force thereof.

* * * * *